United States Patent
Matsumura et al.

[11] Patent Number: 5,935,844
[45] Date of Patent: Aug. 10, 1999

[54] POROUS CELLULOSE CARRIER FOR IMMOBILIZING MICROORGANISMS TO CONVERT NITROGEN COMPOUNDS

[75] Inventors: Masatoshi Matsumura, Tsukuba; Naoyuki Fujii, Fukui, both of Japan

[73] Assignee: Biomaterial Co., Ltd., Fukui, Japan

[21] Appl. No.: 08/624,705

[22] Filed: Mar. 26, 1996

[51] Int. Cl.⁶ .............. B09B 3/00; C12N 11/12; C08B 5/04; C12P 1/00
[52] U.S. Cl. .......... 435/262.5; 435/41; 435/128; 435/179; 536/56
[58] Field of Search .............. 435/41, 128, 179, 435/262.5; 536/56

[56] References Cited

U.S. PATENT DOCUMENTS

| | | | |
|---|---|---|---|
| 4,687,808 | 8/1987 | Jarrett et al. | 525/54.1 |
| 4,756,831 | 7/1988 | Menzel et al. | 210/617 |
| 5,135,542 | 8/1992 | Sasakura et al. | 8/194 |
| 5,200,471 | 4/1993 | Coleman et al. | 525/326.9 |
| 5,298,615 | 3/1994 | Matsui et al. | 536/56 |

FOREIGN PATENT DOCUMENTS

| | | |
|---|---|---|
| 5-23684 | 2/1993 | Japan . |
| 6-7789 | 1/1994 | Japan . |
| 7-68282 | 3/1995 | Japan . |
| 7-68283 | 3/1995 | Japan . |
| 7-68287 | 3/1995 | Japan . |
| 7-68288 | 3/1995 | Japan . |
| 7-68289 | 3/1995 | Japan . |
| 7-68290 | 3/1995 | Japan . |
| 7-68291 | 3/1995 | Japan . |
| 7-68292 | 3/1995 | Japan . |

*Primary Examiner*—David M. Naff
*Attorney, Agent, or Firm*—Morrison&Foerster LLP

[57] ABSTRACT

A carrier for immobilizing microorganisms is prepared by producing a porous cellulose derivative by reacting porous cellulose such as foamed cellulose with a compound selected from the group consisting of a compound having an epoxy group, an N-methylol compound, an imidazolidinone compound, a compound having an aldehyde group, an acetal compound, an active vinyl compound, an aziridinyl compound, a compound having a carboxyl group, a compound having an acyl group, a quaternary ammonium compound, an amidophosphazene compound and a compound having an isocyanate group. The carrier may also be formed by coating the porous cellulose or the porous cellulose derivative with a compound obtained by reacting a compound containing an epoxy group with a polyamine compound. The porous cellulose may have a pore diameter ranging from 30 to 2000 $\mu$m. The carrier may be used in converting harmful nitrogen compounds into harmless compounds in a liquid such potable water or wastewater. The carrier and liquid to be treated are added to a nitrification treatment tank under aerobic conditions and/or a denitrification treatment tank under anaerobic conditions, microorganisms are immobilized on the carrier and nitrogen compounds are converted. The carrier may also be added to other liquid treatment tanks where microorganisms are immobilized for treatment.

31 Claims, 15 Drawing Sheets

Time course of NH4-N conc. in a liquid and the pH

POROUS CELLULOSE CARRIER FOR IMMOBILIZING MICROORGANISMS TO CONVERT NITROGEN COMPOUNDS

FIELD OF THE INVENTION

The present invention relates to a carrier for immobilizing microorganisms, which comprises a porous cellulose derivative, and to a method of converting nitrogen compounds contained in a liquid using the same. More specifically, the invention relates to a carrier for immobilizing microorganisms which comprises a porous cellulose derivative or a porous cellulose, that controls biodegradation due to microorganisms by reacting a wide variety of compounds with cellulose, and to a method which can convert harmful nitrogen compounds contained in potable water or wastewater liquid into harmless ones by introducing the carrier for immobilizing microorganisms into a liquid treatment tank such as a nitrification treatment tank or a denitrification treatment tank.

BACKGROUND OF THE INVENTION

With the recent increase in the consumption of nitrogen fertilizers, the contamination of groundwater and the like with nitrogen compounds such as nitric acid has also increased. For instance, in several cases in European and American countries, young children who had drunk water containing nitrate died of anemic blue baby syndrome. The gastric juice in the stomachs of these young children was not acidic; the nitric acid converted into nitrous acid due to microorganisms in the stomach, and the nitrite bonded to hemoglobin in the blood. Thus, the young children died because of insufficient oxygen supply.

The World Health Organization (WHO) has determined the acceptable standard concentration of nitrate nitrogen to be 10 ppm. However, groundwater in many European and American countries actually far exceeds this standard. For example, approximately 8% of all wells in Denmark have detectable nitrate nitrogen concentrations as high as 50 ppm. Further, nitrate nitrogen concentrations as high as 150 ppm have been detected in groundwater from the United States. Furthermore, because groundwater in some cultivated fields in Japan has been found to contain nitrate nitrogen concentrations in amounts exceeding the standard of 10 ppm, the Japanese Ministry of Public Welfare and Environmental Agency have heightened their monitoring of nitrate nitrogen concentrations.

Further, treatment of wastewater such as sewage has also led to increased eutrophication of lakes and rivers. Despite improvements and amplification of sewer facilities, the fundamental problems have not been solved. An activated sludge treatment has been employed; this treatment can decrease the biochemical oxygen demand (BOD) attributable to microorganisms but cannot remove nutrients such as nitrogen compounds, phosphorus, or the like, which were derived from organic compounds contained in the wastewater. When these nutrients are released into lakes and rivers, plant planktons multiply, eutrophication continues, and the lakes and rivers are further contaminated.

Various methods are applied during drainage of groundwater, wastewater and the like to remove the ammonia nitrogen, nitrate nitrogen and nitrite nitrogen converted from harmful organic nitrogen. In the biochemical denitrification method, treatment occurs in a nitrification treatment tank or a denitrification treatment tank using nitrifying bacteria or denitrifying bacteria present in an activated sludge. The nitrification treatment tank can convert organic nitrogen into ammonia nitrogen, and can also convert the ammonia nitrogen into nitrate nitrogen or nitrite nitrogen using nitrifying bacteria having a slow growth rate. The nitrate nitrogen and nitrite nitrogen which were converted from the ammonia nitrogen in the nitrification treatment tank can be further converted into nitrogen in a denitrification treatment tank using denitrifying bacteria supplied with a hydrogen donor; the nitrogen is thus released into the atmosphere. Thus, nitrogen compounds are removed from groundwater and wastewater. In previous attempts to increase treatment capacity, the introduction of a polyurethane foam or a carrier for immobilizing microorganisms prepared from jelly-like polyethylene glycol derivatives as disclosed in JP-A-5-023684 into the nitrification treatment tank has been proposed. ("JP-A" refers to an unexamined published Japanese patent application.) The use of a cellulose foam as a carrier for immobilizing microorganisms to produce useful material such as citric acid has also been proposed.

However, conventional methods have the following problems. The method of using a carrier prepared from polyethylene glycol derivatives, as disclosed in JP-A-5-023684, requires prior immobilization of microorganisms onto the carrier. This requires a plant investment in an apparatus for immobilizing microorganisms. The carrier prepared from polyethylene glycol derivatives can immobilize nitrifying bacteria thereon in the nitrification treatment tank under aerobic conditions, but cannot immobilize denitrifying bacteria thereon in the denitrification treatment tank under anaerobic conditions. Thus, this conventional method cannot be widely used.

When a polyurethane foam is used in the denitrification treatment tank, it can overcome the disadvantage of the polyethylene glycol derivatives, but the polyurethane foam does not have a sufficient affinity for the above-mentioned microorganisms. Therefore, the maximum nitrification rate of the polyurethane foam carrier used in the nitrification treatment tank is as low as 130 (mg-N/l-carrier/hr); further increases in the treatment capacity are difficult to imagine. In addition, since the polyurethane foam, after use, is synthetic resin, the disposal of the polyurethane foam is problematic.

Further, the cellulose foam has a markedly short life in an environment where cellulose degradation activity is high, and it does not withstand use for several months. Thus, the cellulose foam is not suitable for many purposes.

SUMMARY OF THE INVENTION

Accordingly, one object of the present invention is to provide a carrier for immobilizing microorganisms that can easily immobilize microorganisms in high density, can be used in any liquid treatment tank without limiting the usage sites thereof, and does not require a plant investment for the immobilization of microorganisms.

Another object of the present invention is to provide a method for converting nitrogen compounds contained in a liquid such as potable water or wastewater, which can increase the treatment capacity of a carrier used in a liquid treatment tank such as a nitrification treatment tank or a denitrification tank.

A further object of the present invention is to provide a carrier for immobilizing microorganisms which can be easily disposed by incineration or deposition into a land fill to degrade the carrier, even after its use in a liquid treatment tank.

Thus, the problems present in the prior art can be overcome by the present invention which relates to a carrier for immobilizing microorganisms and comprises a porous cellulose and a porous cellulose derivative.

The present invention also relates to a method of converting nitrogen compounds in a liquid to be treated which comprises: introducing the carrier for immobilizing microorganisms together with a liquid to be treated into a liquid treatment tank under aerobic conditions or anaerobic conditions; stirring the resulting mixture, and thereby converting nitrogen compounds contained in the liquid.

In a preferred embodiment of the present invention, the carrier for immobilizing microorganisms comprises a porous cellulose derivative obtained by reacting at least one member selected from the group consisting of an epoxy compound having an epoxy group, an N-methylol compound, an imidazolidinone compound, an aldehyde compound having an aldehyde group, an acetal compound, an active vinyl compound, an aziridinyl compound, a compound having a carboxyl group, a compound having an acyl group, a quaternary ammonium compound, an amidophosphazene compound, and a compound having an isocyanate group with cellulose.

In a further preferred embodiment of the present invention, the carrier comprises a porous cellulose obtained by coating cellulose with a compound which is obtained by reacting an epoxy compound having an epoxy group with a polyamine compound.

DETAILED DESCRIPTION OF THE INVENTION

Figure 1:
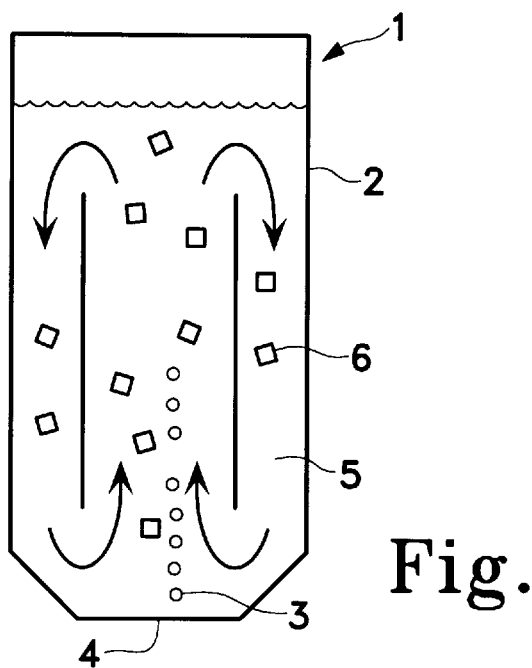
FIG. 1 is a schematic drawing of a tower-like gas lift-type liquid treatment tank.

The porous cellulose derivative which can be used in the present invention is formed by reacting a compound having a functional group with a hydroxyl group of a glucose which is a constituent of cellulose. The compound has a network structure and there is crosslinking between the molecules. The compound can be obtained by reacting at least one member selected from the group consisting of an epoxy compound having an epoxy group, an N-methylol compound, an imidazolidinone compound, an aldehyde compound having an aldehyde group, an acetal compound, an active vinyl compound, an aziridinyl compound, a compound having a carboxyl group, a compound having an acyl group, a quaternary ammonium compound, an amidophosphazene compound, and a compound having an isocyanate group with cellulose. The porous cellulose derivative according to the invention can be obtained by reacting an epoxy compound having an epoxy group with cellulose so that a hydroxyl group in a glucose constituent of cellulose reacts with an epoxy group in the epoxy compound, and the epoxy ring-opens, thereby crosslinking glucose constituents of cellulose. The epoxy compound is reacted in an amount ranging from 3 to 60% by weight, preferably ranging from 5 to 30% by weight, and more preferably ranging from 20 to 30% by weight, based on the weight of the cellulose. If the amount of the epoxy compound is less than 3% by weight, degradation of cellulose by microorganisms is accelerated, and as a result, the carrier cannot be used over a long period of time. On the other hand, if the amount of the epoxy compound exceeds 60% by weight, the cellulose loses its inherent properties as the carrier and is also liable to disintegrate. For those reasons, it is desirable that the epoxy compound be used in an amount that falls within the above-described range.

A specific method for obtaining the porous cellulose derivative by crosslinking cellulose with an epoxy compound is as follows: the cellulose is immersed in a solution prepared by dissolving the epoxy compound into a solvent or into a dispersion prepared by dispersing the epoxy compound into a solvent, and the reaction is conducted at room temperature or under heating.

Solvents which can be used include polar solvents such as water, alcohols, ketones or ethers. These solvents can be used alone or as mixtures thereof. Preferred examples of these solvents include water, ethanol, methanol, isopropyl alcohol, dimethylsulfoxide, and N,N-dimethylformamide. The reaction can be conducted using the solvent at a temperature ranging from 10 to 200° C. when the humidity ranges from 10 to 60% RH, and at a temperature ranging from 50 to 140° C. when the humidity ranges from 60 to 100% RH. Preferably, the reaction time can be controlled by the shape of the cellulose; the reaction time preferably ranges from about 0.5 to 200 minutes, and more preferably ranges from 30 to 60 minutes. If required and necessary, the reaction product can be aged by leaving it at room temperature in order to complete the reaction between the epoxy compound and the cellulose.

It is possible to conduct the reaction in the presence of a catalyst. Examples of a catalyst include sodium hydroxide (NaOH), a Lewis acid such as trifluoroboron ammonia complex, zinc borofluoride ($Zn(BF_4)_2$), and tin tetrachloride ($SnCl_4$). The amount of the catalyst to be added preferably ranges from 1 to 10% by weight based on the weight of the epoxy compound when sodium hydroxide or a Lewis acid such as trifluoroboron ammonia complex is used. The catalyst can be previously added to the solvent or can be added to the solution or dispersion when the cellulose is immersed in the solution or dispersion.

The porous cellulose derivative used in the present invention can be obtained using an epoxy compound represented by the following formulae (2), (3), (4), (5) and (6). The preferred embodiment is an epoxy compound having an epoxy group with at least one member selected from the formula (2), formula (3), formula (4), formula (5) and formula (6) groups.

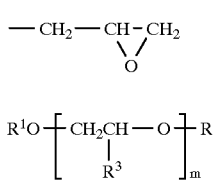

(1)

(2)

In formula (2), m represents an integer ranging from 0 to 50; at least one of $R^1$ and $R^2$ represents the formula (1) group above; $R^1$, $R^2$ and $R^3$ represent a hydrogen atom or a methyl group; and $R^1$ and $R^2$ may be the same or different.

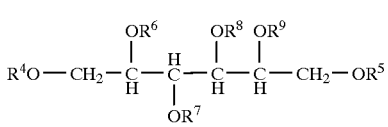

(3)

In formula (3), at least one of $R^4$, $R^5$, $R^6$, $R^7$, $R^8$ and $R^9$ represents the formula (1) group above; and $R^4$, $R^5$, $R^6$, $R^7$, $R^8$, and $R^9$ may be the same or different and may represent a hydrogen atom, a phenyl group or a methyl group.

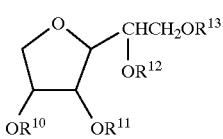

(4)

In formula (4), at least one of $R^{10}$, $R^{11}$, $R^{12}$ and $R^{13}$ represents the formula (1) group above; and $R^{10}$, $R^{11}$, $R^{12}$ and $R^{13}$ may be the same or different and may represent a hydrogen atom, a phenyl group or a methyl group.

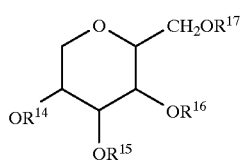

(5)

In formula (5), at least one of $R^{14}$, $R^{15}$, $R^{16}$ and $R^{17}$ represents the formula (1) group above; and $R^{14}$, $R^{15}$, $R^{16}$ and $R^{17}$ may be the same or different and may represent a hydrogen atom, a phenyl group or a methyl group.

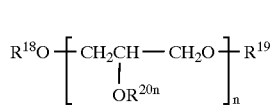

(6)

In formula (6), n represents an integer ranging from 1 to 10; at least one of $R^{18}$, $R^{19}$ and $R^{20n}$ represents the formula (1) group above; and $R^{18}$, $R^{19}$ and $R^{20n}$ may be the same or different and may represent a hydrogen atom, a phenyl group or a methyl group.

It is preferred for an epoxy compound having formulae (2), (3), (4), (5) or (6) as the basic structure to have at least two of the formula (1) groups above. Because the epoxy compound has a plurality of the formula (1) groups, the epoxy groups bond to hydroxyl groups of the glucose constituents of cellulose, and this effectively controls the degradation of the cellulose by microorganisms.

Preferred examples of an epoxy compound are the epoxy compounds represented by formula (2) wherein both $R^1$ and $R^2$ represent formula (1); the epoxy compound represented by formula (3) wherein at least two of $R^4$, $R^5$, $R^6$, $R^7$, $R^8$ and $R^9$ represent formula (1); the epoxy compound represented by formula (4) wherein at least two of $R^{10}$, $R^{11}$, $R^{12}$ and $R^{13}$ represent formula (1); the epoxy compound represented by formula (5) wherein at least two of $R^{14}$, $R^{15}$, $R^{16}$ and $R^{17}$ represent formula (1); and the epoxy compound represented by formula (6) wherein at least two of $R^{18}$, $R^{19}$ and $R^{20n}$ represent formula (1). In particular, in an epoxy compound represented by formulae (3), (4), (5) and (6), it is preferred that the positions to which the formula (1) groups are bonded are far apart. For example, it is preferred in an epoxy compound represented by formula (3) that $R^4$ and $R^5$ are the formula (1) groups.

$R^{20n}$ in formula (6) can be the same or different when the bracketed portion is repeated. For example, when n is 2, the bracketed portion is repeated twice, and as a result, the first $R^{20n}$ is $R^{201}$ and the second $R^{20n}$ is $R^{202}$. The $R^{20n}$s may be the same or different.

More preferred examples of an epoxy compound include the epoxy compound represented by formula (2) wherein m is 0, $R^1$ represents formula (1), and $R^2$ represents a hydrogen atom; the epoxy compound represented by formula (2) wherein m is 5, $R^1$ represents formula (1), $R^2$ represents a phenyl group, and $R^3$ represents a hydrogen atom; the epoxy compound represented by formula (2) wherein m is 1, $R^1$ and $R^2$ each represents formula (1), and $R^3$ represents a hydrogen atom; the epoxy compound represented by formula (3) wherein $R^4$, $R^5$, $R^6$ and $R^9$ each represents formula (1), and $R^7$ and $R^8$ each represents a hydrogen atom; and the epoxy compound represented by formula (6) wherein n is 1, $R^{18}$ and $R^{19}$ each represent formula (1), and $R^{20n}$ represents a hydrogen atom.

Specific examples of an epoxy compound include glycidol, glycerol diglycidyl ether, glycerol triglycidyl ether, polyglycerol polyglycidyl ether, polyethylene glycol diglycidyl ether, ethylene glycol diglycidyl ether, polypropylene glycol diglycidyl ether, sorbitol polyglycidyl ether, sorbitan diglycidyl ether, bis-(2,3-epoxycyclopentyl)-ether, vinylcyclohexanedioxide butadienediepoxide, 1,2-bis-(2,3-epoxy-2-methylpropoxy)-ethane, and 1,1,3-tris-(2,3-epoxypropoxy)-butane. These compounds can be used alone or as mixtures thereof The porous cellulose derivatives obtained by reacting at least one member selected from the group consisting of an N-methylol compound, an imidazolidinone compound, an aldehyde compound having an aldehyde group, an acetal compound, an active vinyl compound, an aziridinyl compound, a compound having a carboxyl group, a compound having an acyl group, a quaternary ammonium compound, an amidophosphazene compound, and a compound having an isocyanate group with cellulose are functional groups of those compounds, similar to that of the epoxy compound reacted with hydroxyl groups of glucose constituents of cellulose to crosslink glucoses to each other.

Examples of a N-methylol compound include dimethyl urea (DMU), methylated trimethylolmelamine (MTMM), dimethylolethylene urea (DMEU), dimethylolmethyl triazone (DMTr), dimethylolethyltriazone, dimethylolhydroxyethyl triazone, methylated dimethylol urone (DMUr), hexamethylol melamine (HMM), dimethylolpropylene urea (DMPU), dimethyloldihydroxyethylene urea (DMDHEU), tetramethylolacetylene diurea (TMADU), 4-methoxy-5-dimethylpropylene urea dimethylol compound (4MO, 5DM, PU), dimethylolmethyl carbamate (DMAC), dimethylolethyl carbamate, dimethylolhydroxyethyl carbamate, dimethylolhydroxyisopropyl carbamate, dimethyloldimnethoxyethylene urea, dimethylolbutylene urea, dimethylol-5-hydroxypropylene urea, dimethylol urone, and tetramethylolethylene bistriazone. These compounds can be used alone or as mixtures thereof.

An example of an imidazolidinone compound which can be used is a compound represented by the following formula (7).

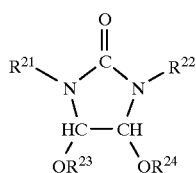

(7)

In formula (7), $R^{21}$ and $R^{22}$ may be the same or different; $R^{21}$ and $R^{22}$ each represent a hydrogen atom, a lower alkyl group, a lower acyl group, an alkoxy group or a —(CH$_2$—CH(CH$_3$)—O—)$_r$—H group wherein r represents an integer ranging from 1 to 3; and $R^{23}$ and $R^{24}$, which may be the same or different, each represent a hydrogen atom, a lower alkyl group, or a lower acyl group.

The lower alkyl group, lower alkoxy group, or lower acyl group in $R^{21}$, $R^{22}$, $R^{23}$, and $R^{24}$ in formula (7) refers to a straight chain or branched functional group having from 1 to 6 carbon atoms, and preferably having from 1 to 4 carbon atoms. Examples of a lower alkyl group include methyl group, ethyl group, n-propyl group, and isopropyl group. In particular, when $R^{21}$ or $R^{22}$ is a lower alkyl group, at least one hydrogen atom in the lower alkyl group can be replaced with hydroxyl group, cyano group, carboxyl group, or lower alkoxycarbonyl group. Specific examples of these substituents include ethoxycarbonyl and carbamoyl. Preferred examples of a substituted lower alkyl group include α-hydroxyethyl, β-hydroxyethyl, β-cyanoethyl, β-carbamoylethyl, β-carboxyethyl, and β-ethoxycarboxyethyl.

Specific examples of an imidazolidinone compound include:
4,5-dihydroxy-imidazolidinone,
1,3-dimethyl-4,5-dihydroxy-2-imidazolidinone,
1,3-diethyl-4,5-dihydroxy-2-imidazolidinone,
1,3-dipropyl-4,5-dihydroxy-2-imidazolidinone,
1,3-di(α-dihydroxyethyl)-4,5-dihydroxy-2-imidazolidinone,
1,3-di(β-dihydroxyethyl)-4,5-dihydroxy-2-imidazolidinone,
1,3-dimethyl-4,5-dimethoxy-2-imidazolidinone,
1,3-dimethyl-4,5-diethoxy-2-imidazolidinone,
1,3-dimethyl-4,5-diisopropoxy-2-imidazolidinone,
1,3-dimethyl-4,5-diacetoxy-2-imidazolidinone,
1,3-di-(β-cyanoethyl)-4,5-dihydroxy-2-imidazolidinone,
1,3-di-(β-cyanoethyl)-4,5-dimethoxy-2-imidazolidinone,
1,3-di-(β-carbamoylethyl)-4,5-dihydroxy-2-imidazolidinone,
1,3-di-(β-carbamoylethyl)-4,5-dimethoxy-2-imidazolidinone,
1,3-di-(β-carboxyethyl)-4,5-dihydroxy-2-imidazolidinone,
1,3-di-(β-carboxyethyl)-4,5-dimethoxy-2-imidazolidinone,
1,3-di-(β-ethoxycarbonylethyl)-4,5-dihydroxy-2-imidazolidinone,
1,3-di-(β-ethoxycarbonylethyl)-4,5-dimethoxy-2-imidazolidinone.

These imidazolidinone compounds can be used alone or as mixtures hereof.

An aldehyde compound having an aldehyde group includes compounds represented by the following formula (9), and specific examples thereof include formaldehyde, glyoxal, acetaldehyde, a compound obtained by reacting a cyclic urea with glyoxal, acrylic aldehyde, and a compound obtained by reacting acrylic amide with glyoxal (acrylic amide-glyoxal reaction product copolymer). These compounds can be used alone or as mixtures thereof.

$$R^{26}(CHO)_x \qquad (9)$$

In formula (9), $R^{26}$ may be absent, but when present it is hydrogen or a hydrocarbon group; the hydrocarbon group has a molecular weight ranging from 14 to 1,000, and may contain oxygen atom, nitrogen atom or sulfur atom. In addition, x is an integer ranging from 1 to 4.

An acetal compound can be obtained by addition reaction of a compound having an aldehyde group or a compound having a ketone group with an alcohol, and includes compounds represented by the following formula (10). Specific examples of an acetal compound include glycol acetal and pentaerythritol bisacetal. These compounds can be used alone or as a mixture thereof.

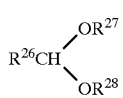

(10)

In formula (10), $R^{26}$ represents a hydrogen or a hydrocarbon group; the hydrocarbon group has a molecular weight ranging from 14 to 1,000, and may contain oxygen atom, nitrogen atom, or sulfur atom. Also, $R^{27}$ and $R^{28}$ each represents a hydrogen or a lower alkyl group.

An active vinyl compound includes compounds represented by the following formula (11). The compound has a double bond therein and has a high reactivity with cellulose. Examples of an active vinyl compound include methacrylic acid hydroxypropyltrimethylammonium chloride, glycerol dimethacrylate, glycerol methacrylate acrylate, glycerol methacrylate alkenylate, diethylene glycol dimethacrylate, trimethylolpropane trimethacrylate, and zinc diacrylate. These compounds can be used alone or as mixtures thereof.

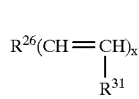 (11)

In formula (11), $R^{26}$ may be absent, but when present is hydrogen or a hydrocarbon group; the hydrocarbon group has a molecular weight ranging from 14 to 1,000, and may contain oxygen atom, nitrogen atom or sulfur atom. Also, $R^{31}$ represents a hydrogen or a methyl group, and x is an integer ranging from 2 to 4.

An aziridinyl compound includes compounds represented by the following formula (12), and examples thereof include diphenyl-methane-bis-4,4'-N,N-diethylene urea, 2,2,4,4,6,6-hexa-(1-aziridinyl)-2,4,6-triphospha-1,3,5-triazine, and 2,2,4,4,6,6-hexa-(1 -aziridinyl)-2,4,6-triphospha-1,3,5-triazine. These compounds can be used alone or as mixtures thereof.

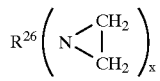 (12)

In formula (12), $R^{26}$ represents a hydrocarbon group having a molecular weight ranging from 14 to 1,000, and may contain oxygen atom, nitrogen atom or sulfur atom. In addition, x is an integer ranging from 2 to 4.

A compound having a carboxyl group includes compounds represented by the following formula (13), and is preferably a poly-carboxylic acid. Examples of these compounds include 1,1,4,4-butane-tetracarboxylic acid, 1,2,3-tricarboxy-2, hydroxy-propane, bis-carboxymethyl ether, and 1,2-bis-carboxyhydroxy ethane. These compounds can be used alone or as mixtures thereof.

 (13)

In formula (13), $R^{26}$ may be absent, but when present is hydrogen or a hydrocarbon group; the hydrocarbon group has a molecular weight ranging from 14 to 1,000, and may contain oxygen atom, nitrogen atom or sulfur atom. In addition, x is an integer ranging from 2 to 4.

A compound having an acyl group includes compounds containing chlorine represented by the following formula (14), and examples thereof include stearic acid chloride, octadecylchloro-carbonic acid ester, and the like. These compounds can be used alone or as mixtures thereof.

 (14)

In formula (14), $R^{26}$ represents a hydrocarbon group having a molecular weight ranging from 14 to 1,000, and may contain oxygen atom, nitrogen atom or sulfur atom; also, x is an integer ranging from 2 to 4.

A quaternary ammonium compound includes compounds represented by the following formula (15), and examples thereof include ethylene glycol bismethylpyridium chloride ether and the like.

 (15)

In formula (15), $R^{26}$ may be absent, but when present is hydrogen or a hydrocarbon group; the hydrocarbon group has a molecular weight ranging from 14 to 1,000, and may contain oxygen atom, nitrogen atom or sulfur atom. Also, $R^{29}$ represents a hydrogen atom or a lower alkyl group, and x is an integer ranging from 2 to 4.

An amidophosphazene compound includes compounds represented by the following formula (8), and examples thereof include an amino-diethylamidophosphazene oligomer, a tetraamino-n-propoxycyclotri-phosphazene, pentaamino-monophenoxycyclotriphosphazene, and the like. These compounds can be used alone or as mixtures thereof.

 (8)

In formula (8), $R^{25}$ represents a lower alkoxy group which may have a substituent, a phenoxy group which may have a substituent, a mono-lower alkylamino group, or a di-lower alkylamino group; where a is an integer of 3 or more, c is an integer of 1 or more, and with the proviso that b+c=2a and b/c≧1.

A compound having an isocyanate group includes compounds represented by the following formula (16), and examples thereof include compounds represented by the formulae (17), (18), and (19) described below. These compounds can be used alone or as mixtures thereof.

 (16)

In formula (16), $R^{26}$ represents a hydrocarbon group having a molecular weight ranging from 14 to 1,000, and may contain oxygen atom, nitrogen atom and sulfur atom; also, x is an integer ranging from 2 to 4.

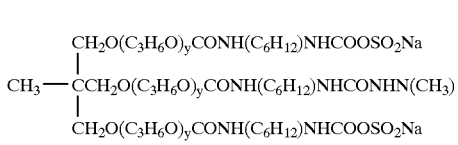 (17)

In formula (17), y is an integer ranging from 2 to 4.

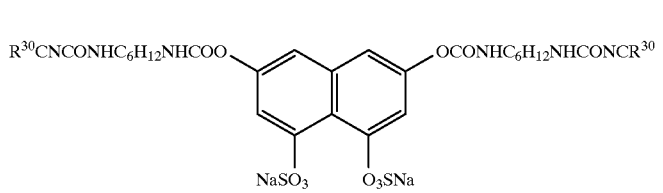

(18)

In formula (18), $R^{30}$ represents a hydrogen atom, an alkyl group, an alkylene group, or a sulfone group.

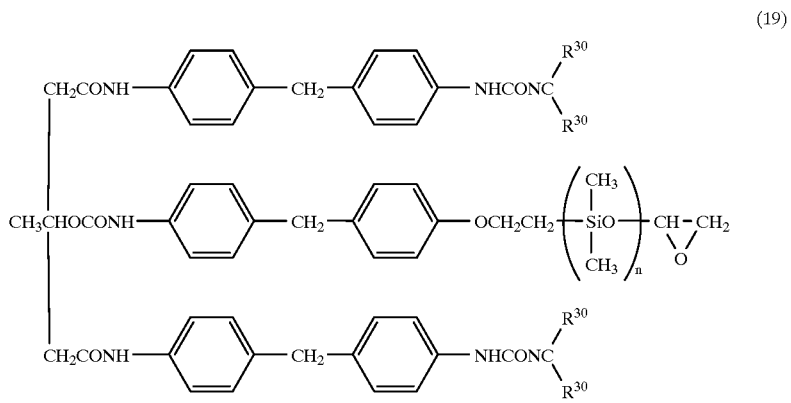

(19)

In formula (19), $R^{30}$ represents a hydrogen atom, an alkyl group, an alkylene group, or a sulfone group; and n is an integer greater than or equal to zero.

At least one member selected from the above-described epoxy compound, N-methylol compound, an imidazolidinone compound, aldehyde compound having an aldehyde group, acetal compound, active vinyl compound, an aziridinyl compound, compound having a carboxyl group, compound having an acyl group, quaternary ammonium compound, amidophosphazene compound, and compound having isocyanate group can be reacted with cellulose in an amount ranging from 3 to 60% by weight, preferably ranging from 15 to 40% by weight, and more preferably ranging from 30 to 40% by weight, based on the weight of cellulose. If the amount of the compound reacted is less than 3% by weight, degradation of cellulose by microorganisms is accelerated and the carrier cannot be used over a long period of time. On the other hand, if the amount of the compound reacted exceeds 60% by weight, the inherent properties of cellulose are lost, and the carrier is liable to disintegrate, leading to deterioration of the strength of the carrier. For these reasons, the compound should be used in an amount that falls within the above-described range.

At least one member selected from the above-described epoxy compound having an epoxy group, N-methylol compound, an imidazolidinone compound, aldehyde compound having an aldehyde group, acetal compound, active vinyl compound, an aziridinyl compound, compound having a carboxyl group, compound having an acyl group, quaternary ammonium compound, amidophosphazene compound, and compound having an isocyanate group can be reacted with cellulose in the following manner: the cellulose is immersed in a solution prepared by dissolving the above-described compound in a solvent or a dispersion prepared by dispersing the compound in a solvent, and the reaction is conducted at room temperature or under heating. Solvents which can be used include polar solvents such as water, alcohols, ketones, or ethers. These solvents can be used alone or as mixtures thereof. Preferred examples of these solvents include water, ethanol, methanol, isopropyl alcohol, dimethylsulfoxide, N,N-dimethyl-formamide, and the like. The reaction is conducted using the solvents at a temperature ranging from 10 to 200° C. when the humidity ranges from 10 to 60% RH, and at a temperature ranging from 50 to 140° C. when the humidity ranges from 60 to 100% RH, respectively. Preferably, the reaction time can be controlled by the shape of the cellulose. The reaction time preferably ranges from about 0.5 to 200 minutes, and more preferably ranges from 30 to 60 minutes. If desired and necessary, the reaction product can be aged by leaving it at room temperature in order to complete the reaction between the epoxy compound and the cellulose.

The reaction between the above-described compound and the cellulose can be conducted in the presence of a catalyst. Examples of a catalyst which can be used include an inorganic acid and an organic acid. Specific examples of an inorganic acid which can be used include hydrochloric acid (HCl), nitric acid ($HNO_3$), and the like. Examples of an organic acid which can be used include acetic acid ($CH_3COOH$), glycolic acid, oxalic acid and the like. Further examples of a catalyst which can be used include magnesium chloride ($MgCl_2$), zinc chloride ($ZnCl_2$), zinc nitrate ($ZnNO_3$), zinc borofluoride ($Zn(BF_4)_2$), magnesium borofluoride ($Mg(BF_4)_2$), ammonium chloride ($NH_4Cl$), alkanol amine, 2-methyl-2-aminopropanol hydrochloride, secondary ammonium phosphite, ammonium rhodanate, and the like.

The amount of the catalyst to be added preferably ranges from 3 to 12% by weight based on the weight of the above-described compound. The catalyst can be previously added to the solvent or can be added to the solution or the dispersion when the cellulose is immersed therein.

Further, a method can be employed where at least one member selected from the epoxy compound having an epoxy group, the N-methylol compound, the aldehyde compound, the aldehyde compound having an aldehyde group, the acetal compound, the active vinyl compound, the aziridinyl compound, the compound having a carboxyl group, the compound having an acyl group, the quaternary ammonium compound, the amidophosphazene compound, and the compound having an isocyanate group, is added to a viscose liquid having dissolved therein cellulose in an amount falling within the above-described range, a pore-forming material is added thereto, and the resulting mixture is introduced into an appropriate mold and coagulated therein under heating, thereby obtaining a foamed porous cellulose derivative.

According to another embodiment of the present invention, the carrier for immobilizing microorganisms comprises a porous cellulose obtained by coating cellulose with a compound obtained by reacting an epoxy compound having an epoxy group with a polyamine compound. By coating the cellulose with such a compound, the cellulose chains are protected from enzymes which degrade cellulose, which are found in microorganisms. The compound obtained by reacting the epoxy compound having an epoxy group with the polyamine compound is coated on the cellulose in an amount ranging from 10 to 60% by weight, preferably ranging from 15 to 50% by weight, and more preferably ranging from 20 to 35% by weight, based on the weight of the porous cellulose. The polyamine compound is reacted with the epoxy compound in an amount ranging from 20 to 150% by weight, preferably ranging from 30 to 120% by weight, and more preferably ranging from 80 to 120% by weight, based on the weight of the epoxy compound. If the amount of the compound obtained by reacting the epoxy compound with the polyamine compound and coated on the cellulose is less than 10% by weight, the degradation of the cellulose by microorganisms is accelerated, and as a result, the carrier cannot be used over a long period of time. On the other hand, if the amount of the compound coated is more than 60% by weight, the specific gravity of the coated porous cellulose increases, the ability of the carrier to flow in a liquid treatment tank becomes poor, and it is difficult to increase the treatment capacity. For these reasons, it is desirable for the compound to be coated in an amount that falls within the above-described range.

The above-described porous cellulose derivative can be used as the cellulose to be coated. For example, the porous cellulose derivative can be obtained by reacting at least one member selected from an epoxy compound having an epoxy group, an N-methylol compound, an imidazolidinone compound, an aldehyde compound having an aldehyde group, an acetal compound, an active vinyl compound, an aziridinyl compound, a compound having a carboxyl group, a compound having an acyl group, a quaternary ammonium compound, an amidophosphazene compound, and a compound having an isocyanate group with cellulose.

Examples of a polyamine compound include a polyethyleneimine, a polyallylamine, a polyvinylamine, and the like.

The porous cellulose derivative or porous cellulose that has been reacted or coated can prevent degradation by microorganisms and therefore can be used over a long period of time in a liquid treatment tank such as a nitrification tank or a denitrification tank.

The cellulose which can be used in the present invention is preferably a porous cellulose and more preferably a foamed cellulose. The shape of the cellulose can be spherical, cylindrical, a hollow cylindrical shape, or a dice shape. The individual carriers are of a size to allow their functionality as described herein. They preferably fall within a size range from about 1 mm$^3$ to about 125,000 mm$^3$, more preferably falling within a size range from about 1 mm$^3$ to about 8,000 mm$^3$, and most preferably falling within a size range from about 1 mm$^3$ to about 1,000 mm$^3$. The foamed cellulose can be obtained by chemically treating pulps having a high purity to convert the pulps into viscose which can be dissolved in an organic solvent, adding a pore-forming material thereto, introducing the resulting mixture into an appropriate mold, and heating to coagulate the same. The pores can be open cells or closed cells depending on the type of treating liquid. Open cell refers to a structure where the pores present in the foamed cellulose are continuously connected; closed cell refers to a structure where each pore is surrounded by septa. It is more preferable to use the foamed cellulose having open cells. The cellulose which is preferably used is one having a pore diameter, or standard size of the pore, ranging from 30 to 2,000 $\mu$m, preferably ranging from 50 to 2,000 $\mu$m, and more preferably ranging from 50 to 300 $\mu$m. The pore diameter can be measured by various methods; cellulose having a pore diameter ranging from 30 to 2,000 $\mu$m, measured by any measurement method, can be used in the present invention.

The method of converting nitrogen compounds in a liquid using the carrier for immobilizing microorganisms, comprising the porous cellulose derivative or the porous cellulose according to the present invention includes the following embodiments.

One embodiment is a method of converting nitrogen compounds in a liquid, which comprises: introducing the carrier for immobilizing microorganisms together with a liquid to be treated into a nitrification treatment tank under aerobic conditions, a denitrification treatment tank under anaerobic conditions, or a liquid treatment tank; and stirring the resulting mixture, thereby converting nitrogen compounds in the liquid to be treated.

Another embodiment is a method of converting nitrogen compounds in a liquid, which comprises: introducing the carrier for immobilizing microorganisms together with a liquid to be treated into a nitrification treatment tank under aerobic conditions and a denitrification tank under anaerobic conditions; stirring the resulting mixture; and converting the nitrogen compounds in the liquid while flowing the entire amount of the liquid from the nitrification treatment tank under aerobic conditions to the denitrification treatment tank under anaerobic conditions.

A further embodiment is a method of converting nitrogen compounds in a liquid, which comprises: introducing the carrier for immobilizing microorganisms together with a liquid to be treated into a nitrification tank under aerobic conditions and a denitrification treatment tank under anaerobic conditions; stirring the resulting mixture; flowing the entire amount of the liquid from the nitrification treatment tank under aerobic conditions into the denitrification treatment tank under anaerobic conditions; and converting the nitrogen compounds in the liquid while circulating part of the liquid between the nitrification treatment tank under aerobic conditions and the denitrification treatment tank under anaerobic conditions.

The "liquid to be treated" according to the present invention refers to a liquid that contains nitrogen compounds which are to be converted into other nitrogen compounds. Examples of a liquid to be treated include groundwater, wastewater, sewage, and the like.

The "nitrogen compounds" contained in the liquid to be treated according to the present invention are compounds containing nitrogen atom. Examples thereof include ammonia, nitrate, nitrite, and the like, which are mainly contained in the nitrification treatment tank and the denitrification treatment tank. Further examples of these nitrogen compounds include proteins, amino acids, and the like, which are contained in an aeration tank used for BOD removal.

The "liquid treatment tank" refers to a treatment tank for treating a liquid containing nitrogen compounds which are to be converted. Examples of a liquid treatment tank include a purification tank to be used in a sewage treatment plant or the like, an aeration tank to be used in a wastewater treatment, a nitrification tank, a denitrification tank, and the like.

The "nitrification treatment tank," which is particularly used for wastewater treatment, refers to a liquid treatment tank that can convert organic nitrogen into ammonia nitrogen, and further into nitrate nitrogen or nitrite nitrogen, by the action of nitrate oxidizing bacteria or nitrite oxidizing bacteria under aerobic conditions. In general, microorganisms that perform the nitrification treatment already exist in a liquid treatment tank. When a nitrification treatment tank is prepared by omitting the carbon sources which are the nutrients for microorganisms, selection of microorganisms occurs. As a result, microorganisms such as nitrate oxidizing bacteria or nitrite oxidizing bacteria that can perform nitrification treatment are present in the majority. When the carrier for immobilizing microorganisms, which comprises the porous cellulose derivative or the porous cellulose according to the present invention, is introduced into the tank during the above process, the microorganisms that perform nitrification treatment are immobilized onto the carrier and the capacity of the nitrification treatment can be markedly increased in comparison to the capacity achieved through conventional methods. Genus Nitrosomonas is an example of a nitrite oxidizing bacteria that can be used to perform the nitrification treatment in a nitrification tank; genus Nitrobacter is an example of a nitrate oxidizing bacteria that can perform an important role in nitrification treatment in a nitrification tank.

The denitrification treatment tank can be used in combination with the nitrification tank for the wastewater treatment, or can be used in the treatment of groundwater containing a large amount of nitrate; the treatment is preferably conducted under anaerobic conditions. The porous cellulose derivative or the porous cellulose of the present invention is introduced into the denitrification treatment tank to immobilize denitrifying bacteria in a similar manner as in the nitrification treatment tank, and nitrate is converted into nitrogen gas. Thus, nitrogen compounds are removed from the liquid to be treated. Examples of denitrifying bacteria include genus Pseudomonas, genus Micrococcus, genus Spirillum, Achromobacter, genus Alcaligenes, genus Hydrogenomonas, genus Tiobacillus, and the like.

A hydrogen donor can be introduced into the denitrification tank. Examples of a hydrogen donor which can be used include methanol, acetic acid, ethanol, acetone, glucose, methyl ethyl ketone, isopropyl alcohol, and the like. The hydrogen donor supplies hydrogen for the conversion of nitrate nitrogen or nitrite nitrogen into nitrogen gas ($N_2$) and water ($H_2O$).

According to the present invention, nitrogen compounds can be removed by first treating the treatment tank liquid in a nitrification treatment tank, followed by treating the liquid in a denitrification treatment tank. Thus, the liquid containing nitrite nitrogen or nitrate nitrogen which has been treated in the above-described nitrification treatment tank, is introduced into a denitrification treatment tank to convert nitrite nitrogen or nitrate nitrogen into nitrogen gas; this removes nitrogen compounds from the liquid to be treated. Alternatively, a settling basin may be disposed between the nitrification treatment tank and the denitrification treatment tank; the liquid to be treated flows from the nitrification treatment tank, is introduced into the settling basin, and is then introduced into the denitrification treatment tank to remove nitrogen compounds in the liquid. Further, according to the invention, an aeration tank may be disposed before the nitrification treatment tank so as to introduce the liquid to be treated into the aeration tank; this decreases the BOD in the liquid. The liquid thus treated is introduced into the settling basin and is thereafter introduced into the nitrification treatment tank to remove nitrogen compounds in the liquid. Furthermore, part of the liquid, which has been treated in the treatment tank, first in the nitrification treatment tank and then in the denitrification treatment tank, can be circulated into the denitrification tank to be further treated therein. Moreover, nitrogen compounds contained in the liquid to be treated can be removed by disposing the settling basin between the denitrification tank and the nitrification tank and treating the liquid therein.

The liquid treatment tanks may contain the porous cellulose derivative or the porous cellulose in an amount ranging from 3 to 100 vol % based on the volume of the treatment tanks; the amount varies depending on the shape of the treatment tank. It is desirable for the nitrification treatment tank to contain the porous cellulose derivative or the porous cellulose in an amount ranging from 3 to 30 vol %, preferably ranging from 5 to 25 vol %, and more preferably ranging from 10 to 20 vol %, based on the volume of the nitrification treatment tank. If the amount of the porous cellulose derivative or the porous cellulose is less than 3 vol %, the treatment capacity decreases. On the other hand, if the amount thereof exceeds 100 vol %, the ability of the liquid to flow is markedly impaired, and the treatment efficiency is markedly decreased. For the above reasons, it is preferred to use the porous cellulose derivative or the porous cellulose in an amount that falls within the above-described range. Further, in the denitrification treatment tank, the carrier can be used as filling, for example, as in a column. In this case, the amount of the carrier which can be filled into the tank is from 50 to 100 vol % based on the volume of the treatment tank.

The present invention relates to a carrier for immobilizing microorganisms, comprising a porous cellulose derivative or a porous cellulose, and a method of converting nitrogen compounds contained in a liquid using the carrier, where one or more members selected from an epoxy compound having an epoxy group, an N-methylol compound, an imidazolidinone compound, an aldehyde compound having an aldehyde group, an acetal compound, an active vinyl compound, an aziridinyl compound, a compound having a carboxyl group, a compound having an acyl group, a compound having an isocyanate group, a quaternary ammonium compound, and amidophosphazene compound crosslinks glucose constituents of cellulose, thereby reducing or preventing the disintegration of cellulose due to enzymes which decompose cellulose, which are found in microorganisms.

Further, by coating the cellulose with the compound obtained by reacting the epoxy compound with the polyamine compound, the cellulose is protected, thereby making it difficult for microorganisms that contain enzymes which decompose cellulose to contact the cellulose; as a result, decomposition of the cellulose can be prevented.

When the carrier for immobilizing microorganisms, comprising the porous cellulose derivative is immersed into the liquid treatment tank such as a nitrification treatment tank or a denitrification treatment tank together with the liquid to be treated, and the resulting mixture is stirred therein, a large amount of the microorganisms are immobilized on the carrier due to the inherent characteristics of the cellulose; as a result, the activity of the microorganisms can be maintained.

Further, when the carrier for immobilizing microorganisms comprising the porous cellulose is introduced into a liquid treatment tank such as a nitrification treatment tank or a denitrification treatment tank together with the liquid to be treated, and the resulting mixture is stirred therein, cationic charges possessed by the compound obtained by reacting the epoxy compound with the polyamine compound immobilize a large amount of microorganisms onto the carrier; as a result, the density of the microorganisms can be increased.

The present invention is explained in more detail with reference to the following specific embodiments.

Figure 2:
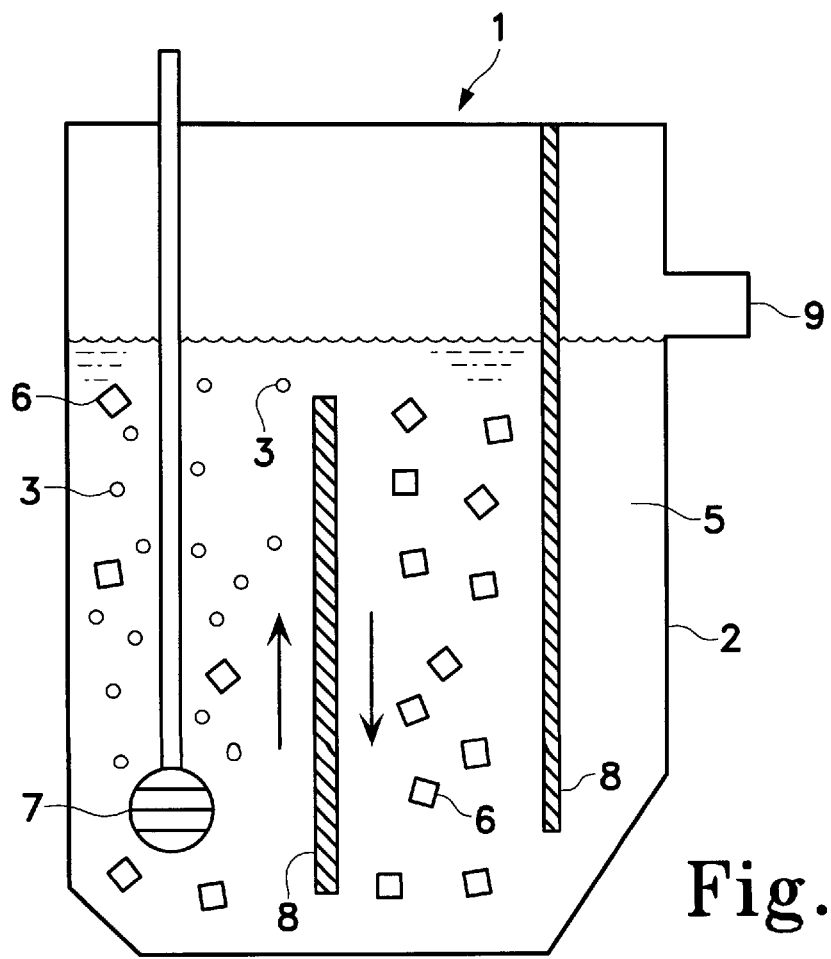
FIG. 2 is a schematic drawing of a box-like gas lift-type liquid treatment tank.
Figure 3:
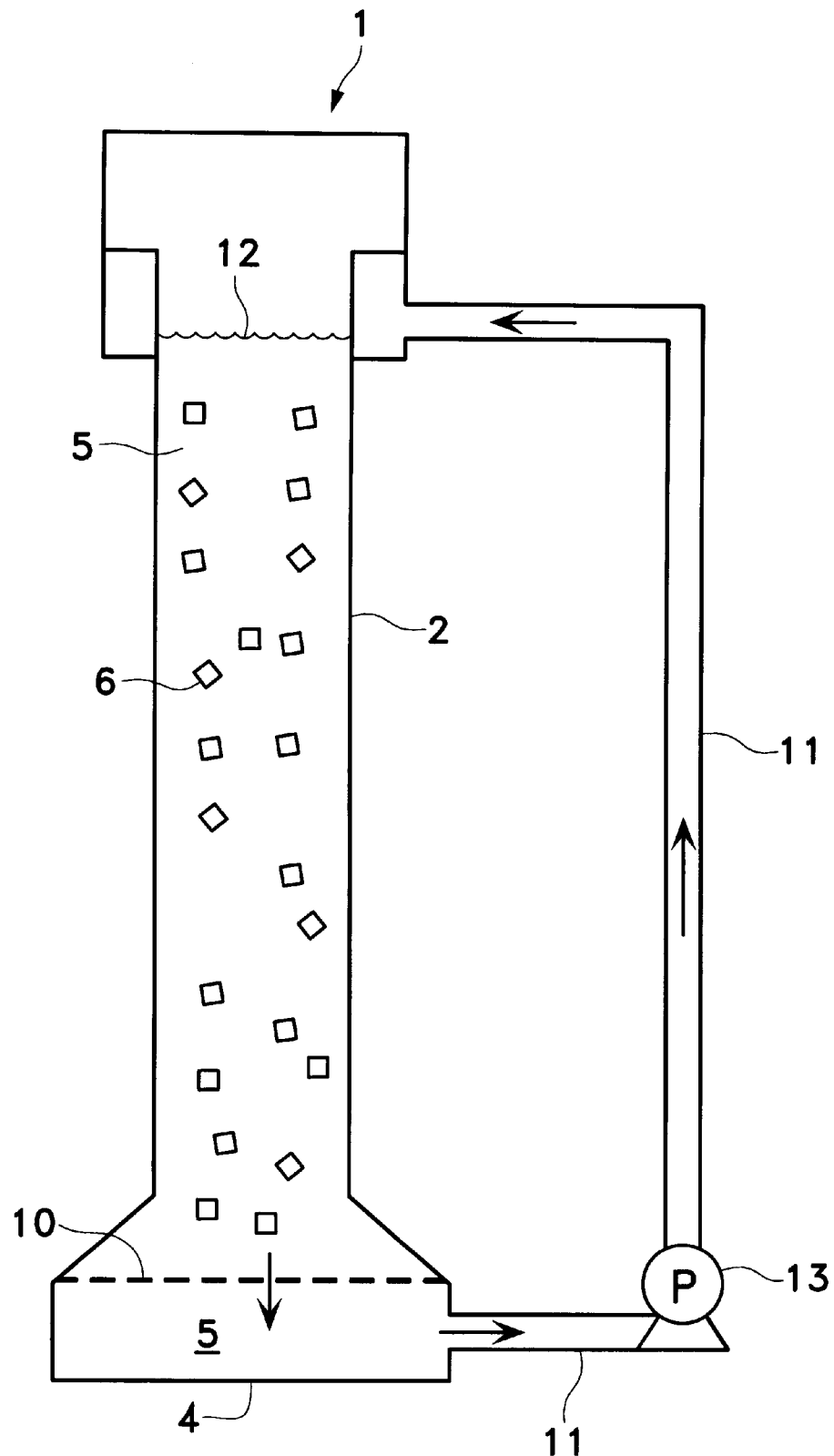
FIG. 3 is a schematic drawing of a downward-flowing expanding-type liquid treatment tank.
Figure 4:
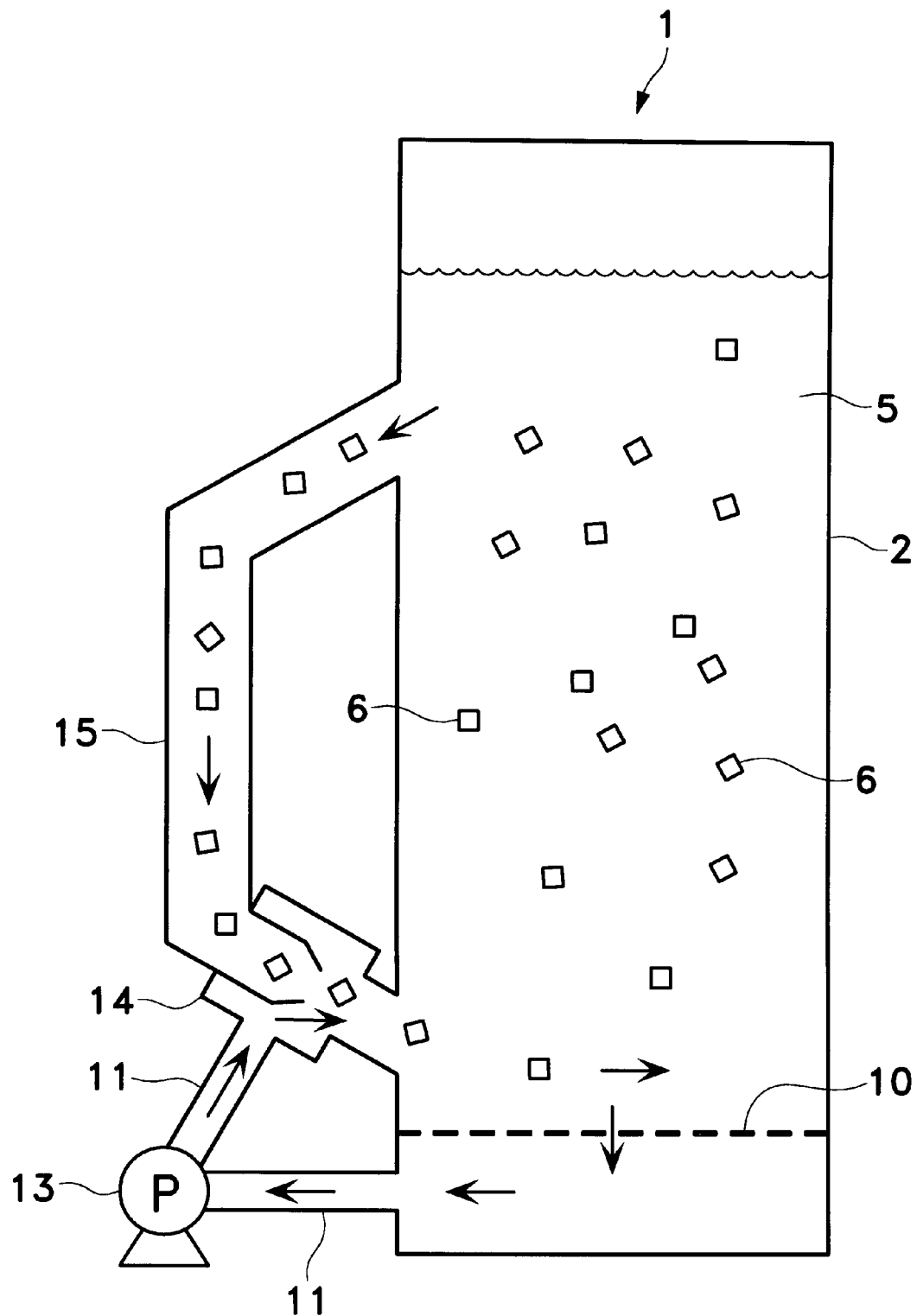
FIG. 4 is a schematic drawing of an ejector-type liquid treatment tank.
Figure 5:
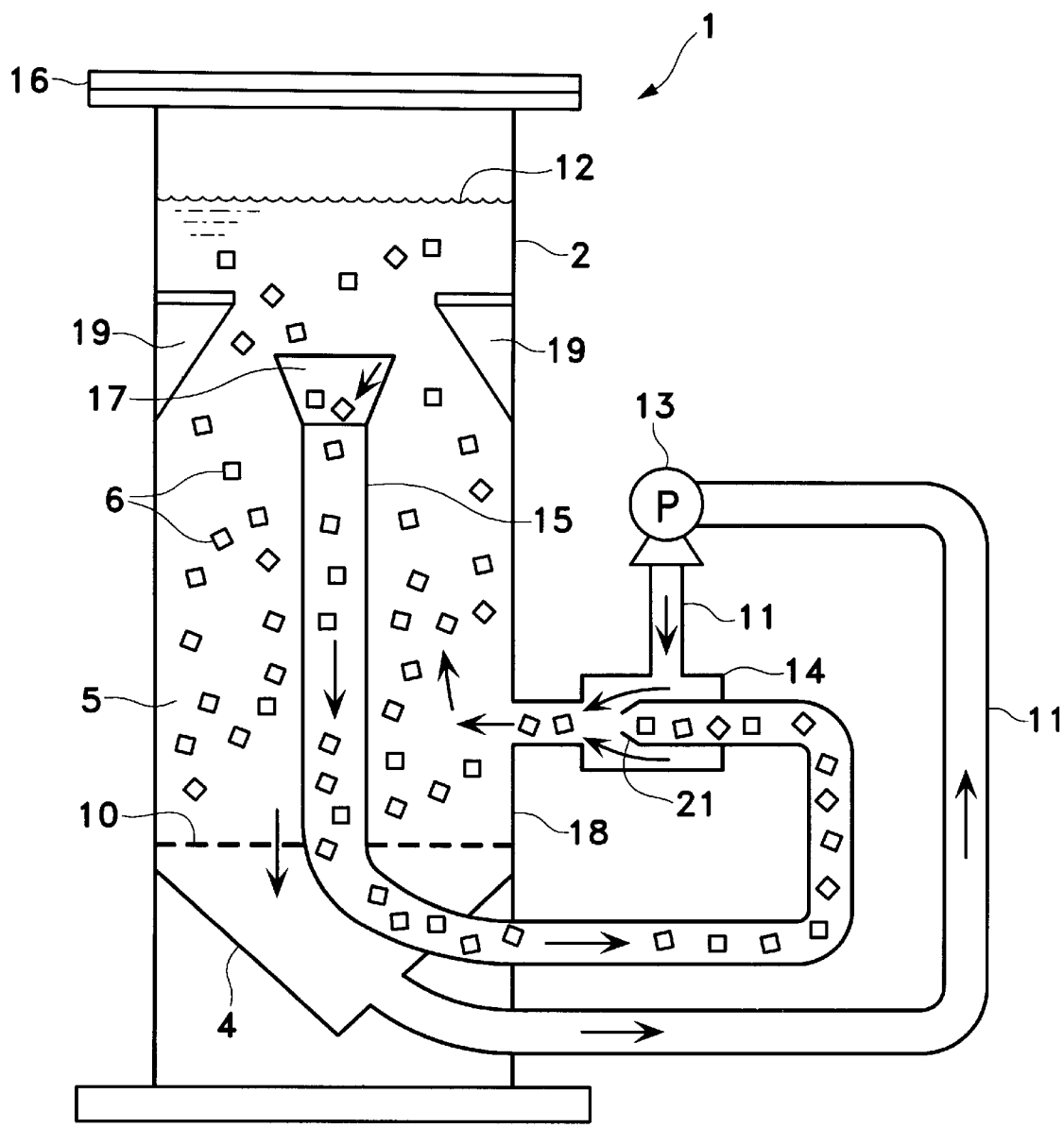
FIG. 5 is a schematic drawing of another ejector-type liquid treatment tank.
Figure 6:
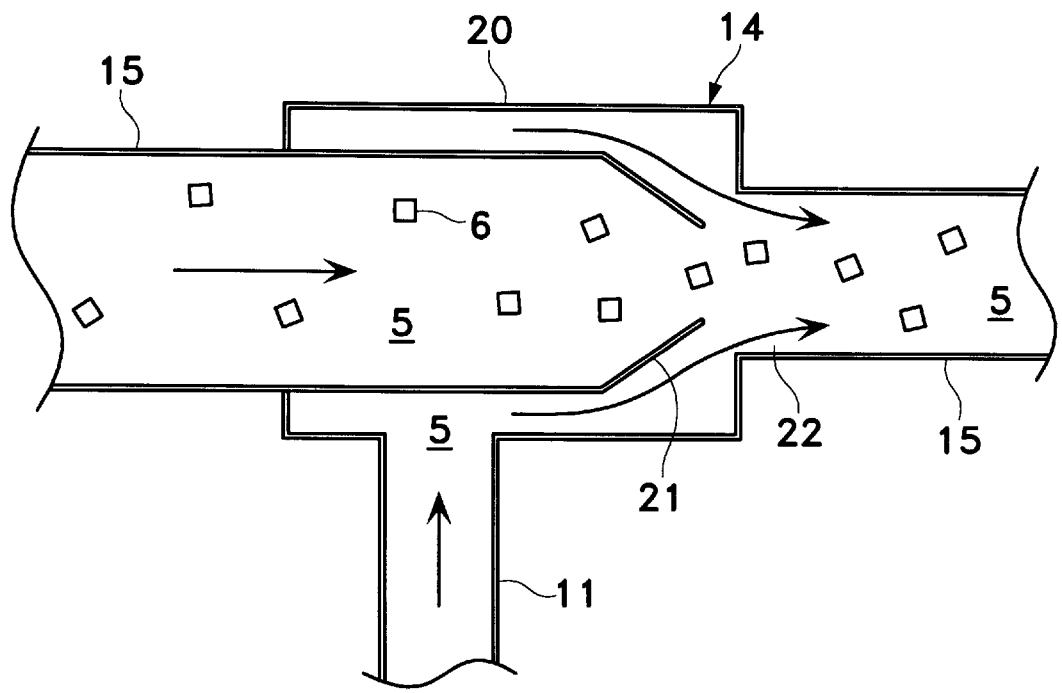
FIG. 6 is a schematic drawing of a liquid current jet device.

Specific examples of a liquid treatment tank which can be used in the present invention include conventional liquid treatment tanks as shown in FIGS. 1 to 4, and the liquid treatment tank as shown in FIG. 5. FIGS. 1 and 2 exemplify the liquid treatment tanks that can stir a carrier for immobilizing microorganisms (hereinafter simply referred to as a "carrier") and a liquid to be treated by introducing a gas thereinto. FIGS. 3, 4 and 5 show a liquid treatment tank where the stirring of the liquid to be treated and the carrier in the tanks is performed by circulating the liquid in the tank. In particular, the liquid treatment tanks shown in FIGS. 4 and 5 include a liquid current jet device as shown in FIG. 6, which can stir the liquid to be treated together with the carrier.

A detailed description of the respective liquid treatment tanks will be made hereinafter.

FIG. 1 shows a tower-like gas lift-type liquid treatment tank (1). In this embodiment, the introduction of a gas (3) such as nitrogen gas, air, or the like from the bottom (4) of the liquid treatment tank (1) causes a stirring action, or upward and downward flow, inside of the tank body (2) as indicated by the arrows in the figure; thus, a liquid (5) to be treated and a carrier (6) can be stirred to achieve completion of treatment. In the tank shown in FIG. 1, a stirring means such as propellers can be employed in the tank body (2) to stir the liquid (5) to be treated.

FIG. 2 shows a box-like gas lift-type liquid treatment tank (1). In this liquid treatment tank (1), a gas supply means (7) supplies a gas (3) from an air compressor or a nitrogen tank into the liquid (5) to be treated; thus, treatment under aerobic or anaerobic conditions can be achieved by introducing a gas (3) such as air into the liquid (5). After treatment, the liquid can be withdrawn through a partition wall (8) via an outlet (9). A stirring action, or upward and downward flow, occurs as indicated by the arrows, in the same manner as in the tank shown in FIG. 1, resulting in completion of treatment.

FIG. 3 shows a downward-flowing expanding-type liquid treatment tank (1). The tank is mainly used under anaerobic conditions, and stirring is conducted by flowing the liquid (5) to be treated downward. The liquid treatment tank (1) has a screen (10) which partitions the lower inside portion of the tank into two parts. The screen (10) separates the carrier (6) from the liquid (5), and thereby prevents the carrier (6) from entering into a reflux pipe (11) connected to the lower portion below the screen (10). The reflux pipe (11) is located outside the tank and is connected to the bottom (4) of the tank; the reflux pipe (11) is also connected to the tank body (2) at a position that is higher than the liquid level (12) in the tank body (2). A pump (13) circulates the liquid (5) to be treated to effectuate a stirring, thereby completing the treatment.

FIG. 4 shows an ejector-type liquid treatment tank (1). The liquid treatment tank is partitioned into an upper portion and a lower portion by a screen (10). The lower portion below the screen (10) has a reflux pipe (11) connected to a pump (13) which circulates the liquid (5) to be treated. A carrier recovery pipe (15) located outside of the tank is connected to a liquid current jet device (14) that joins the reflux pipe (11). The pump (13) forces the liquid (5) to flow through the reflux pipe (11) into the liquid current jet device (14) to form a liquid current jet. The liquid current jet causes a driving force in the tank body (2), circulates the carrier (6) and liquid (5) through the carrier recovery pipe (15), and thereby effectuates a fluidized stirring.

FIG. 5 shows another embodiment of the tank shown in FIG. 4, i.e., another example of the ejector-type liquid treatment tank having a liquid current device (14). The liquid treatment tank (1) has a carrier recovery pipe (15), a reflux pipe (11) having a circulating pump (13) in the middle thereof, and a liquid current jet device (14).

The tank body (2) is an airtight, cylindrical vessel having a bottom (4) and a lid (16) The tank body (2) has a screen (10) which partitions the inside thereof into two portions. The screen (10) separates the carrier (6) from the liquid (5) to be treated and prevents the carrier (6) from entering into a reflux pipe (11). The carrier recovery pipe (15) of the tank body (2) has a carrier recovery port (17) at its upper edge. The carrier recovery pipe (15) sucks the carrier (6) and the liquid (5) from a position slightly below the liquid level (12) of the liquid (5), through a tank wall (18) to the outside of the tank body (2). The carrier recovery pipe (15) is joined to the reflux pipe (11) via a liquid current jet device (14).

The reflux pipe (11) is connected to a pump (13) that forces the liquid (5) in the tank body (2) into the liquid current jet device (14); the driving force of the liquid current jet generated by the liquid current jet device (14) circulates the liquid (5) and the carrier (6) through the carrier recovery pipe (15). The inside of the tank body (2) has slanted walls (19) around part of or the entire periphery of the carrier recovery port (17). The carrier (6) that floats toward the liquid level (12) can easily be collected around the periphery of the carrier recovery port.

The theory of the liquid current jet device (14) used in FIGS. 4 and 5 is explained using FIG. 6. A box (20) in the reflux pipe (11) receives the carrier recovery pipe (15). A leading-out edge (21) of the carrier recovery pipe (15) faces a narrow diameter portion (22) of the box (20). When the liquid (5) to be treated is introduced into the box (20) and passes through the narrow diameter portion (22), the flow rate of the liquid is accelerated. As a result, the periphery of the narrow diameter portion (22) is under negative pressure; the suction from this negative-pressure allows the liquid (5) containing the carrier (6) to form a liquid current jet when it emerges from the carrier recovery pipe (15).

The liquid treatment tank (1) described above preferably uses an airtight tank body (2); a water jacket can also be provided at the periphery of the tank body to maintain the liquid (5) at constant temperature. Further, if required and necessary, the following can be provided on the upper portion of the tank body (2) or the tank wall (18), depending on the type of the liquid (5) to be treated: an oxygen electrode and dissolved oxygen meter to measure the dissolved oxygen in the liquid (5); a pH electrode and pH meter to measure pH of the liquid (5); a supply port to supply hydrocarbon, inorganic compounds, and the like; and a device to discharge gas (3), and the like, generated from the liquid (5). Preferable carbon sources which can supply hydrogen atom include methanol and the like. Inorganic compounds which can be used to adjust the pH of the liquid (5) include sodium hydroxide or hydrochloric acid.

The nitrification treatment tank and the denitrification treatment tank used in the present invention are explained in detail below.

Figure 7:
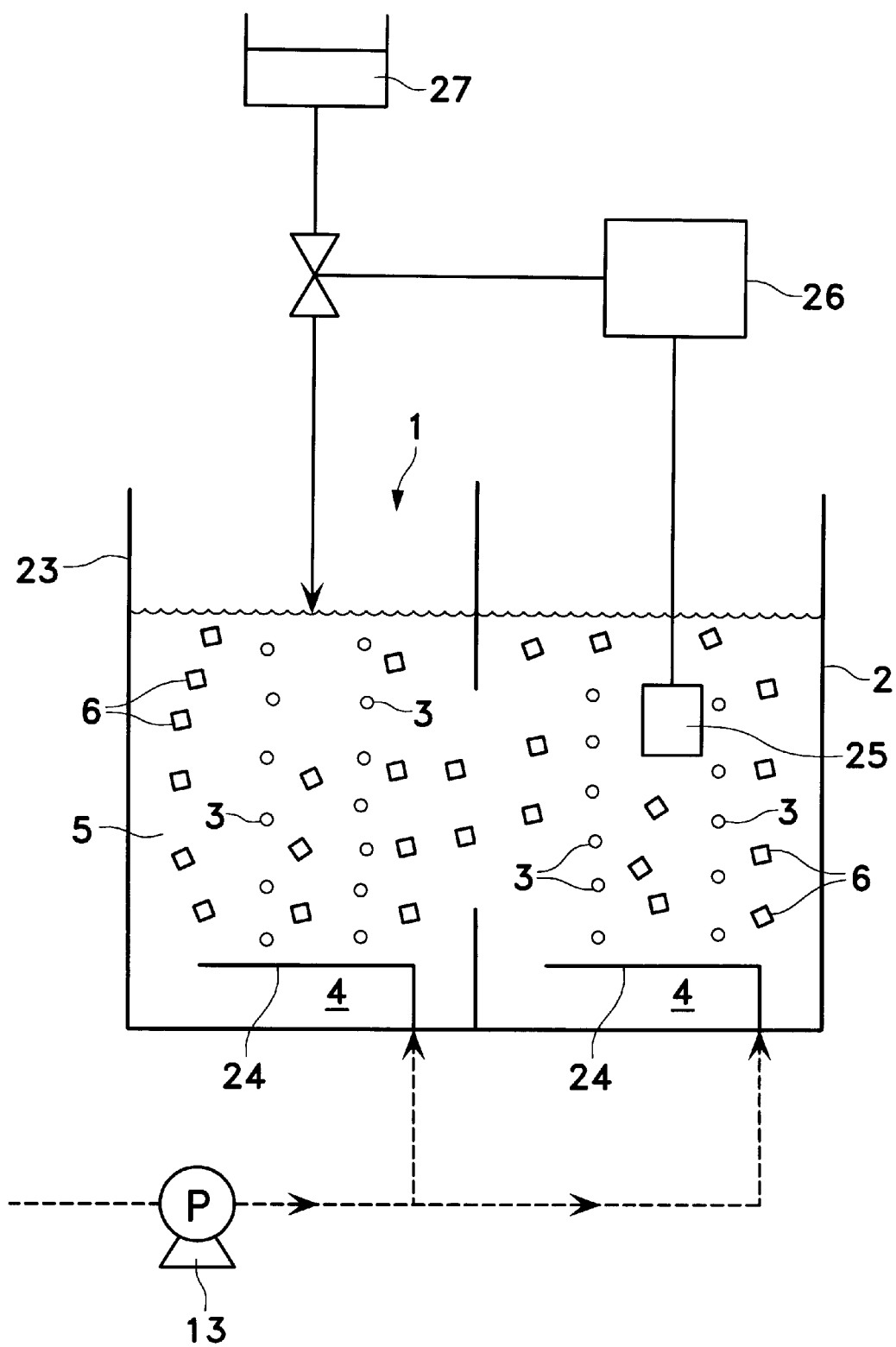
FIG. 7 is a schematic drawing of a liquid treatment tank which is used as a nitrification tank.

The nitrification treatment tank preferably uses a liquid treatment tank (1) shown in FIGS. 1 to 5. When the treatment in the liquid treatment tank (1) is conducted under aerobic conditions, the microorganisms which can perform the nitrification treatment (hereinafter "nitrifying bacteria") multiply, and nitrification treatment can occur. The theory of nitrification is explained by referring to FIG. 7. A blower (24) connected to the pump (13) stirs and supplies air, and is disposed at the bottom (4) of the nitrification treatment tank (23). The tank contains the liquid (5) to be treated, which contains nitrifying bacteria, and the carrier comprising the porous cellulose derivative or the porous cellulose of the present invention. Nitrifying bacteria contained in the liquid (5) are adhered or bonded to the carrier (6) contained in the tank. When the blower (24) feeds air into the liquid (5) and causes a stirring action that increases the contact efficiency between the liquid (5) and the carrier (6), the liquid (5) is nitrified. Further, in the case of nitrification, a pH blower (24) and a pH meter (26) are disposed in the nitrification tank (23) to maintain a constant pH. An alkaline compound (27) such as sodium hydroxide can be introduced as indicated by the arrow, so that the nitrification treatment can be conducted while preventing a decrease in pH; the growth environment of microorganisms can thus be maintained constant. Nitrogen compounds such as ammonia nitrogen ($NH_4$-N) which are present in the liquid (5) to be treated in the nitrification tank (23) are converted into nitrate nitrogen ($NO_3$-N) and nitrite nitrogen ($NO_2$-N).

Figure 8:
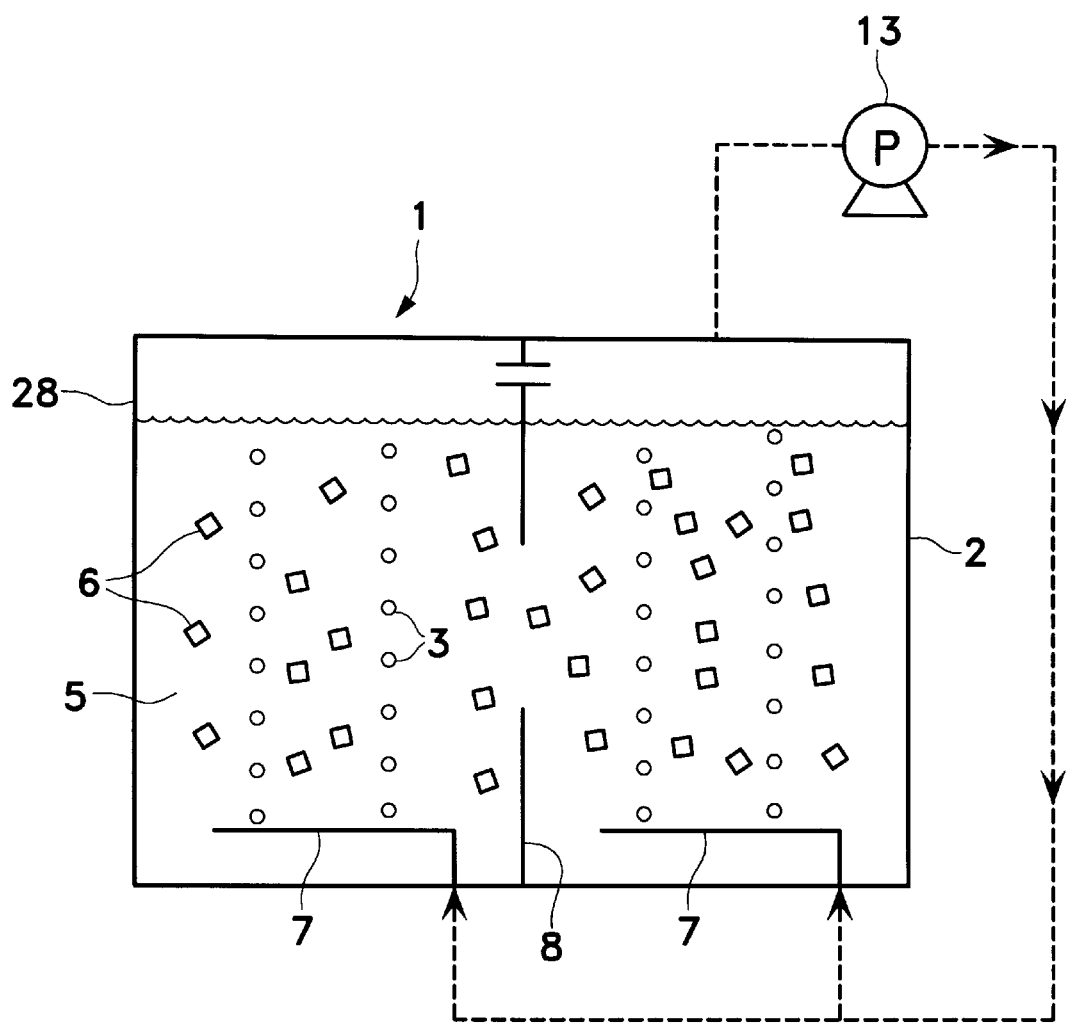
FIG. 8 is a schematic drawing of a liquid treatment tank which is used as a denitrification tank.

Similarly, the liquid treatment tanks (1) shown in FIGS. 1 to 5 can also be employed in a denitrification tank (28) shown in FIG. 8. The theory of denitrification is explained by referring to FIG. 8. When the treatment is conducted in the liquid treatment tank (1) under anaerobic conditions, i.e., oxygen-free conditions, the microorganisms which perform denitrification (hereinafter "denitrifying bacteria") that are in the liquid (5) multiply. A denitrification tank (28) preferably uses a closed tank that can prevent contamination by oxygen. The carrier (6) comprising the porous cellulose derivative or the porous cellulose, and the liquid (5) to be treated are contained in the denitrification tank (28), where denitrifying bacteria adhere or bond to the carrier (6); nitrate nitrogen ($NO_3$-N) and nitrite nitrogen ($NO_2$-N) contained in the liquid (5) are converted into water and nitrogen gas. Denitrification is completed when the nitrogen gas is separated from the denitrification tank (28) and released into the atmosphere; nitrogen compounds are thus removed from the liquid. If desired and necessary, a hydrocarbon such as ethanol, which is a hydrogen donor, can be supplied to the liquid (5) to be treated. Further, the treatment in the denitrification tank (28) can be conducted while using a gas supply means (7) connected to a pump (13) to introduce oxygen-free gas such as nitrogen gas into the liquid (5).

Figure 9:
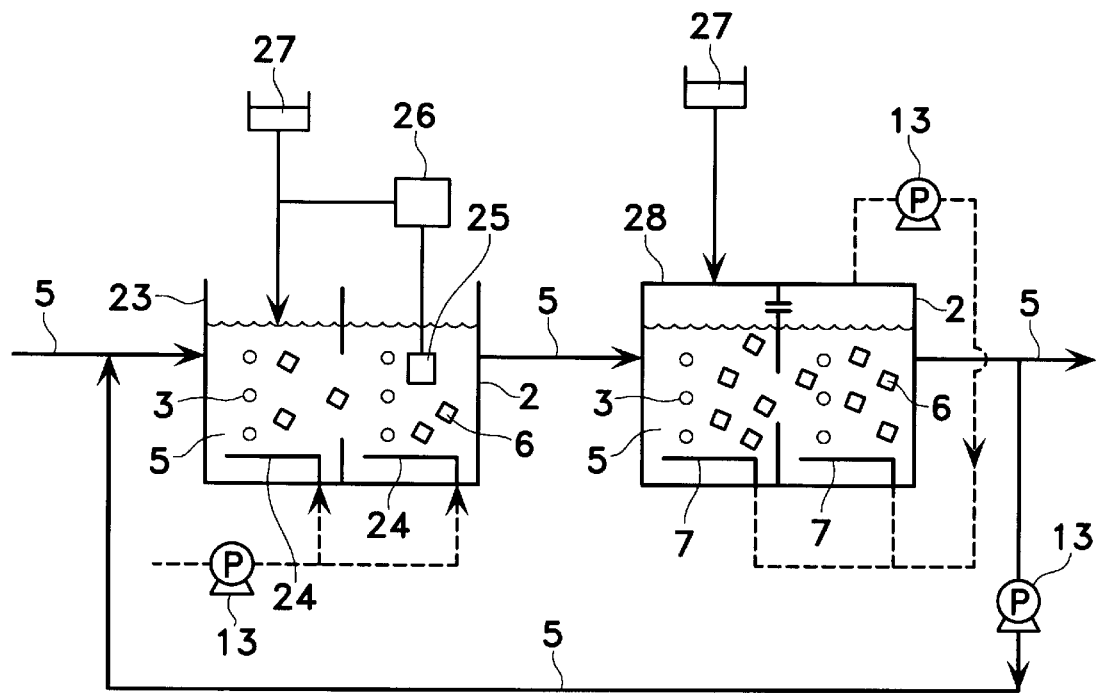
FIG. 9 is a schematic drawing of a liquid treatment tank in which a nitrification tank and a denitrification tank are concurrently used.

The nitrification tank (23) and the denitrification tank (28) can be combined for the treatment of the liquid (5). This method is shown in FIG. 9. A nitrification tank (23) under aerobic conditions and a denitrification tank (28) under anaerobic conditions are disposed in the configuration shown in FIG. 9. Each tank contains the liquid (5) to be treated and the carrier (6) comprising the porous cellulose derivative or the porous cellulose. In the nitrification tank (23), nitrifying bacteria are immobilized when these microorganisms adsorb or adhere onto the carrier (6). Similarly, in the denitrification tank (28), denitrifying bacteria are immobilized when these microorganisms adsorb or adhere onto the carrier. Thus, nitrogen compounds in the liquid (5) in the nitrification tank (23) are converted from ammonia nitrogen ($NH_4$-N) to nitrate nitrogen ($NO_3$-N) and nitrite nitrogen ($NO_2$-N). The liquid (5) is transferred into the denitrification tank (28) where nitrate nitrogen ($NO_3$-N) and nitrite nitrogen ($NO_2$-N) are converted into nitrogen gas and water by the denitrifying bacteria, when a compound (27) such as hydrocarbon is supplied.

Figure 10:
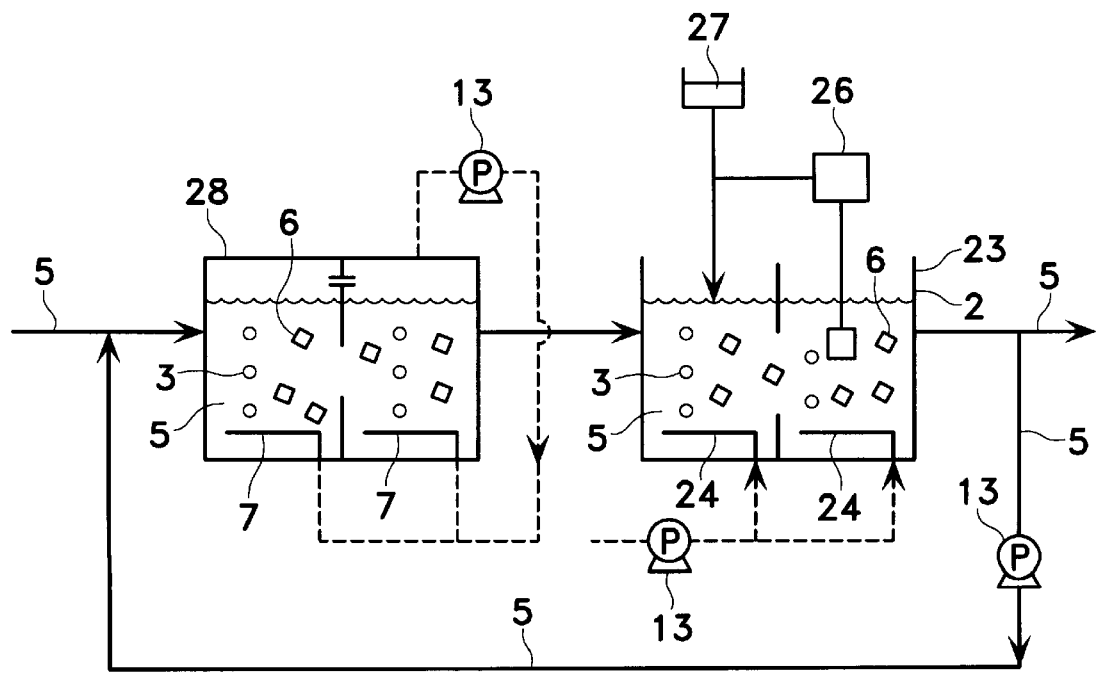
FIG. 10 is a schematic drawing of another liquid treatment tank in which a nitrification tank and a denitrification tank are concurrently used.

In FIG. 10, a denitrification tank (28) and a nitrification tank (23) are disposed in the reverse configuration of that shown in FIG. 9. Each tank contains the liquid (5) to be treated and the carrier (6) comprising the porous cellulose derivative or the porous cellulose used to conduct the treatment. Here, organic compounds such as hydrocarbon contained in the liquid (5) function as hydrogen donors. The nitrate nitrogen ($NO_3$-N) and nitrite nitrogen ($NO_2$-N) contained in the liquid (5) are converted into water and nitrogen gas by the denitrifying bacteria; the nitrogen compounds are thus removed from the liquid. The liquid (5) is then transferred into the nitrification tank (23), and ammonia nitrogen ($NH_4$-N) is converted into nitrate nitrogen ($NO_3$-N) and nitrite nitrogen ($NO_2$-N) in the same manner as described above. Part of the liquid (5) is returned to the denitrification tank (28) and treatment is conducted in the same manner as described above. Nitrogen compounds contained in the liquid (5) are further converted into nitrogen gas and water; the nitrogen compounds are thus removed from the liquid.

The present invention is described in more detail with reference to the following examples showing the preparation of the carrier for immobilizing microorganisms and the conversion of nitrogen compounds contained in the liquid in the nitrification tank and the denitrification tank using the carrier. It should however be understood that the invention is not construed as being limited to the examples. Unless otherwise indicated, all percents, parts, ratios, and the like are by weight.

EXAMPLES 1 TO 4

A carrier composed of a porous cellulose derivative was prepared using an epoxy resin compound in the following manner.

Four types of carriers having different bonding amounts were prepared using 5 to 30% glycerol diglycidyl ether of an epoxy compound. 50 g of a mixed solution composed of glycerol diglycidyl ether in a concentration of 5 to 30%, ethanol aqueous solution in a concentration of 20%, and thorium in a concentration of 1% were prepared. 10 g of foamed products (a cube of 5×5×5 mm having a pore size of 100 μm) were immersed in the resulting mixed solution; the reaction was conducted in a reaction vessel at 121° C. for 15 minutes. Unreacted sodium hydroxide, ethanol and glycerol diglycidyl ether were removed to obtain a carrier composed of a porous cellulose derivative. The actual bonding amount of the glycerol diglycidyl ether was obtained by subtracting the amount of the porous cellulose derivative before the reaction from the weight of the porous cellulose after the reaction; thus, a bonding amount per 10 g of the cellulose was obtained. The carrier obtained in Example 1 had a binding amount of about 0.3 g (about 3%). The carrier obtained in Example 2 had a bonding amount of about 0.7 g (about 7%). The carrier obtained in Example 3 had a bonding amount of about 1.8 g (about 18%). The carrier obtained in Example 4 had a bonding amount of about 3.0 g (about 30%).

EXAMPLE 5

A carrier composed of the porous cellulose derivative and having a bonding amount of about 1.7 g (about 17%) was obtained in the same manner as in Examples 1 to 4, except that cellulose foamed products (a cube of 5×5×5 mm) having a pore diameter of 50 μm were used.

EXAMPLE 6

A carrier composed of the porous cellulose derivative and having a bonding amount of about 1.7 g (about 17%) was obtained in the same manner as in Examples 1 to 4, except that cellulose foamed products (a cube of 5×5×5 mm) having a pore diameter of 500 μm were used.

EXAMPLE 7

A carrier composed of the porous cellulose derivative and having a bonding amount of about 1.7 g (about 17%) was obtained in the same manner as in Examples 1 to 4, except that cellulose foamed products (a cube of 5×5×5 mm) having a pore diameter of 1,260 μm were used.

EXAMPLES 8 TO 11

Four types of the carriers having different bonding amounts were prepared using 1,3-dimethyl-4,5-dihydroxy-2-imidazoridinone. 10 g of cellulose foamed products (a cube of 10×10×10 mm having a pore diameter of 1,260 μm) were immersed in 50 g of a mixed solution of 1,3-dimethyl-4,5-dihydroxy-2-imidazoridinone in a concentration of 5 to 30%, and zinc borofluoride in a concentration of 0.3 to 3%. The reaction was conducted in the same manner as in Examples 1 to 4. The cellulose foamed products thus treated were pre-dried at 110° C. for 5 minutes, subjected to heat treatment at 130° C. for 15 minutes, and washed with water to obtain a carrier composed of the porous cellulose derivative. The bonding amount of the 1,3-dimethyl-4,5-dihydroxy-2-imidazoridinone was measured by subtracting the amount of the porous cellulose derivative before the reaction from the weight of the porous cellulose after the reaction. The carrier obtained in Example 8 had a bonding amount of about 0.3 g (about 3%). The carrier obtained in Example 9 had a bonding amount of about 0.8 g (about 8%). The carrier obtained in Example 10 had a bonding amount of about 1.6 g (about 6%). The carrier obtained in Example 11 had a bonding amount of about 2.8 g (about 28%).

EXAMPLE 12

A carrier was obtained in the same manner as in Examples 8 to 11, except that a melamine-formaldehyde resin represented by formula (20), an N-methylol compound, and 2-methyl-2-aminopropanol hydrochloric acid salt as a catalyst were used. The bonding amount in the carrier was measured in the same manner as in Examples 8 to 11 and was found to be about 0.7 g (about 7%).

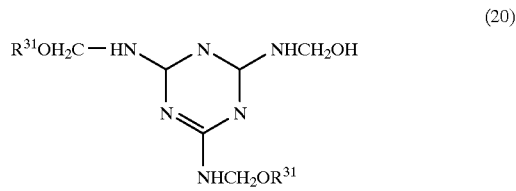

(20)

In formula (20), $R^{31}$ represents an alkyl group.

EXAMPLE 13

A carrier was obtained in the same manner as in Examples 8 to 11, except that a cyclic urea-glyoxal reaction product represented by formula (21), an aldehyde compound, was used. The bonding amount in the carrier was measured in the same manner as in Examples 8 to 11, and was found to be about 1.5 g (about 15%).

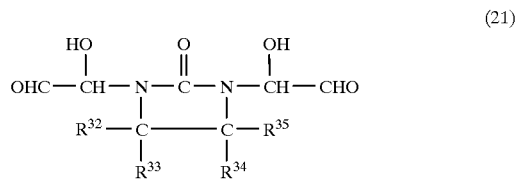

(21)

In formula (21), $R^{32}$, $R^{33}$, $R^{34}$ and $R^{35}$ each represents H, OH, $OR^{36}$ or $COOR^{36}$, wherein $R^{36}$ represents an alkyl group.

EXAMPLE 14

A carrier was obtained in the same manner as in Examples 8 to 1 1, except that diphenylmethane-bis-4,4'-N,N-diethylene urea represented by formula (22), an aziridinyl compound, was used. The bonding amount in the carrier was measured in the same manner as in Examples 8 to 11, and was found to be about 1.2 g (about 12%).

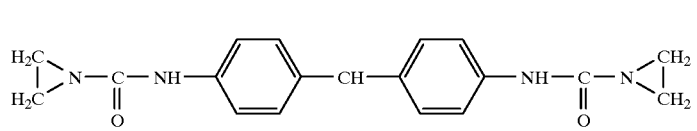

(22)

EXAMPLE 15

A carrier composed of cellulose having coated thereon a compound obtained by reacting an epoxy compound with a polyamine compound was prepared in the following manner. 50 g of an aqueous solution composed of a polyethylene imine having a molecular weight of 70,000 in a concentration of 2.8%, and ethyleneglycol diglycidyl ether in a concentration of 3.3% were prepared. 10 g of cellulose foamed products (a cube of 5×5×5 mm having a pore diameter of 100 μm) were uniformly immersed in the aqueous solution, and allowed to stand for 2 hours. The products thus treated were dried in an oven at 80 to 90° C., and then heated in a thermostat at 120° C. for 30 minutes. After completion of the reaction, the products were washed with tap water, dewatered, washed with ion-exchanged water, and then dried in a thermostat at 60° C. to obtain a carrier. The amount of the reaction product coated was about 3.1 g (about 31%).

Biodegradation Inhibition Test

A biodegradation inhibition test was conducted on the carriers obtained in Examples 1 to 4. The measurement method was as follows. A cellulase solution was prepared by adding cellulase (trade name: R10, a product of Yakult Co., Ltd.) to a citric acid-sodium phosphate buffer solution having pH of 4.5 such that the concentration thereof was 0.5%. The carrier obtained in Example 1 was added to the buffer solution. A L-type test tube containing the resulting mixture was shaken at 72 revolutions per minute in a mono-type shaking apparatus, and the time required for the cellulose to degrade was measured. The cellulase solution was exchanged with a fresh solution twice a week. Untreated cellulose foamed product was used as a control.

The results obtained are shown in Table 1 below.

TABLE 1

|  | Degradation time (hours) | Biodegradation Inhibition Ratio |
|---|---|---|
| Example 1 | 38 | 9 |
| Example 2 | 350 | 87 |
| Example 3 | 1000 or more | 250 or more |
| Example 4 | 2000 or more | 500 or more |
| Example 5 | 1000 or more | 250 or more |
| Example 6 | 1000 or more | 250 or more |
| Example 7 | 1000 or more | 250 or more |
| Example 8 | 40 | 10 |
| Example 9 | 165 | 40 |
| Example 10 | 300 | 75 |
| Example 11 | 800 | 200 |
| Example 12 | 75 | 19 |
| Example 13 | 200 | 50 |
| Example 14 | 120 | 30 |
| Example 15 | 1000 or more | 250 or more |
| Control | 4 | 1 |

It is clear from the data shown in Table 1 that the carriers obtained in Examples 1 to 15 were resistant to cellulase and sufficiently inhibited degradation.

Nitrification Test: Conversion of Nitrogen Compounds Contained in a Liquid in a Nitrification Tank Under Aerobic Conditions Using a Carrier Comprising a Porous Cellulose Derivative A box-like gas lift-type liquid treatment tank (1) shown in FIG. 2 was used as a nitrification tank. When ammonia nitrogen ($NH_4$-N) in a liquid was converted into other nitrogen compounds using each of the carriers for immobilizing microorganisms obtained in Examples 3, 5, 6 and 7, residual amounts of ammonia nitrogen were measured. The details thereof are described in Examples 16 to 19 below.

EXAMPLE 16

Figure 11:
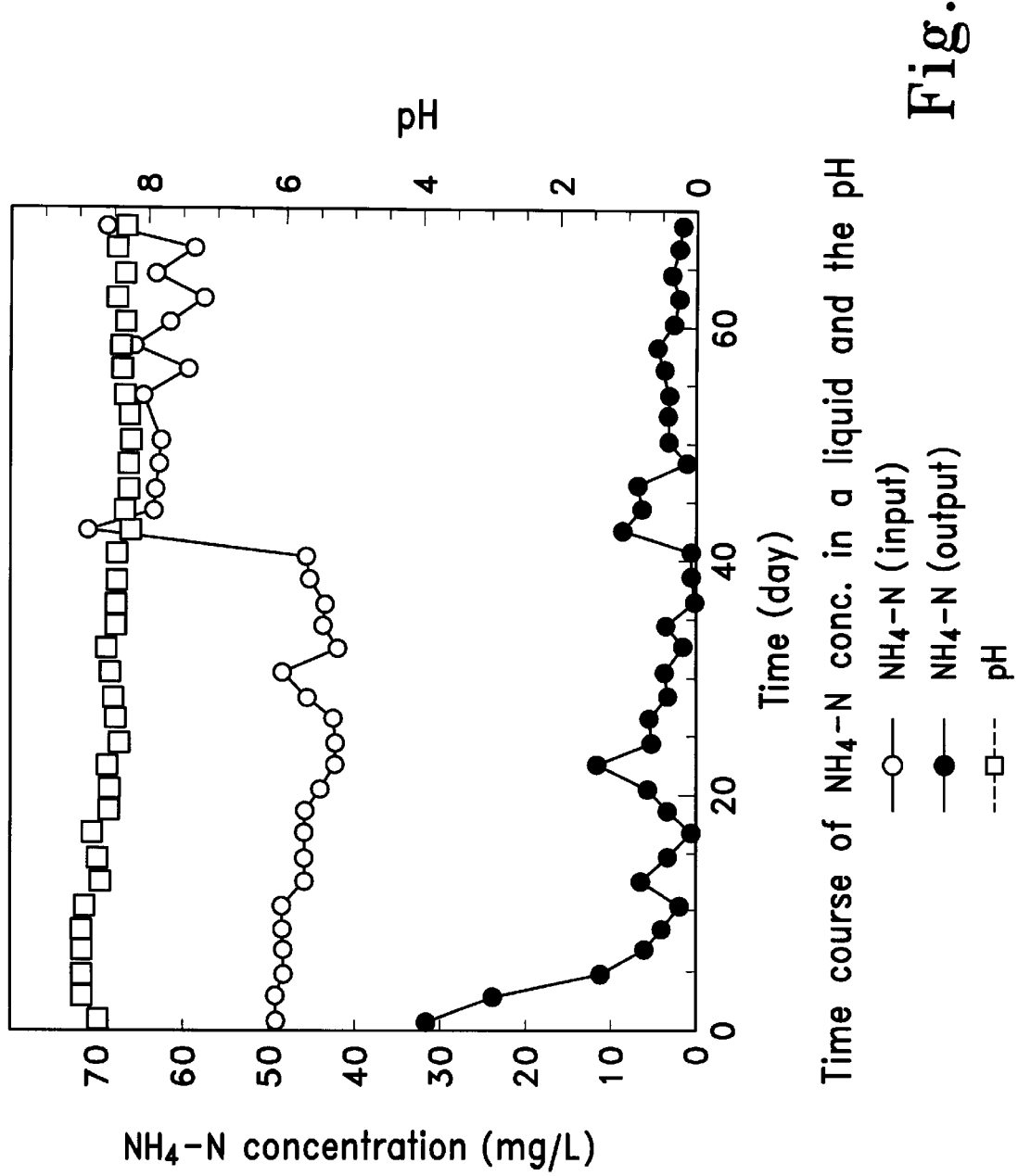
FIG. 11 is a graph showing the measurement of residual ammonia nitrogen ($NH_4$-N) in a liquid which was subjected to nitrification treatment using the box-like gas lift-type liquid treatment tank.

A 3 liter volume liquid treatment tank as shown in FIG. 2 was used as the nitrification treatment tank. An artificially synthesized inorganic wastewater having compositions shown in Table 2 below was prepared. Activated sludge was adsorbed and immobilized onto the porous cellulose derivative used in Example 3 to prepare the carrier. The artificially synthesized inorganic wastewater prepared above was treated with the carrier in the nitrification tank for 70 days while adjusting the pH of the wastewater at around 8.0. The concentrations of ammonia nitrogen ($NH_4$-N) introduced and ammonia nitrogen ($NH_4$-N) discharged were measured. The measurement was conducted under the condition that the amount of dissolved oxygen was 4 mg/ml. The maximum treatment amount in one day was 36 liters, and the treatment amount per one hour was 1,200 ml. The carrier comprising the porous cellulose derivative was introduced into the nitrification tank in the amount of 10 vol % based on the volume of the nitrification tank, and the amount of ammonia nitrogen ($NH_4$-N) introduced was changed to 70 mg/l after 40 days. The treatment capacity of the carrier was 315 mg-N/l-carrier/hr. The results obtained are shown in FIG. 11.

TABLE 2

| Compositions | Amount (mg/l) |
|---|---|
| $NH_4Cl$ [1] | 158.2 |
| $NaHPO_4.12H_2O$ | 23.1 |
| NaCl | 10.1 |
| KCl | 4.7 |
| $CaCl_2.2H_2O$ | 4.7 |
| $MgSO_4.7H_2O$ | 16.7 |
| $NaHCO_3$ | 937.2 |

[1] $NH_4$—N = 40 mg/l

EXAMPLE 17

Figure 12:
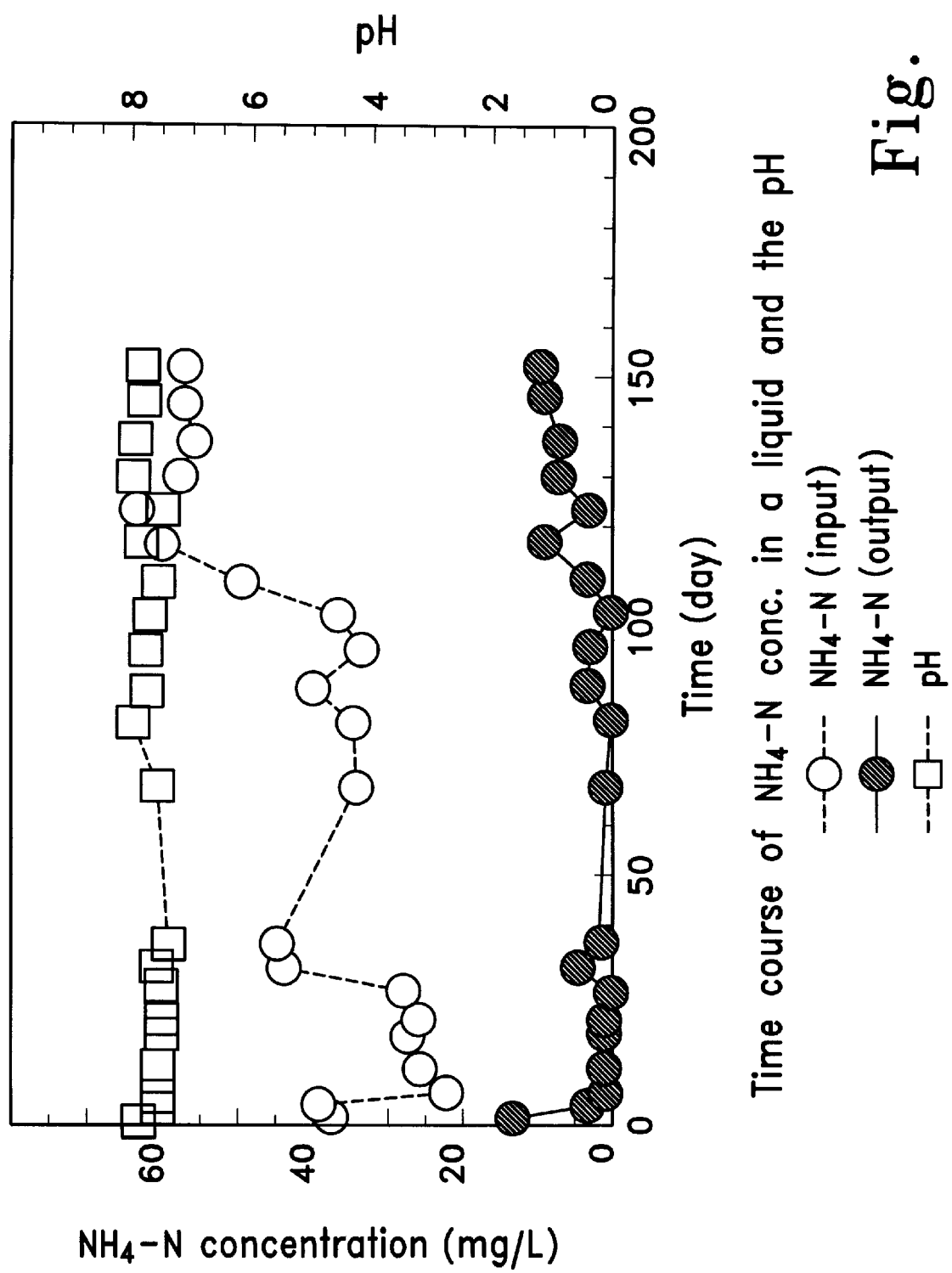
FIG. 12 is a graph showing the measurement of residual ammonia nitrogen ($NH_4$-N) in a liquid which was subjected to nitrification treatment using a carrier having a pore diameter of 50 μm.

A nitrification test was conducted for 150 days in the same manner as in Example 15, except that the carrier obtained in Example 5 was used. The results obtained are shown in FIG. 12.

EXAMPLE 18

Figure 13:
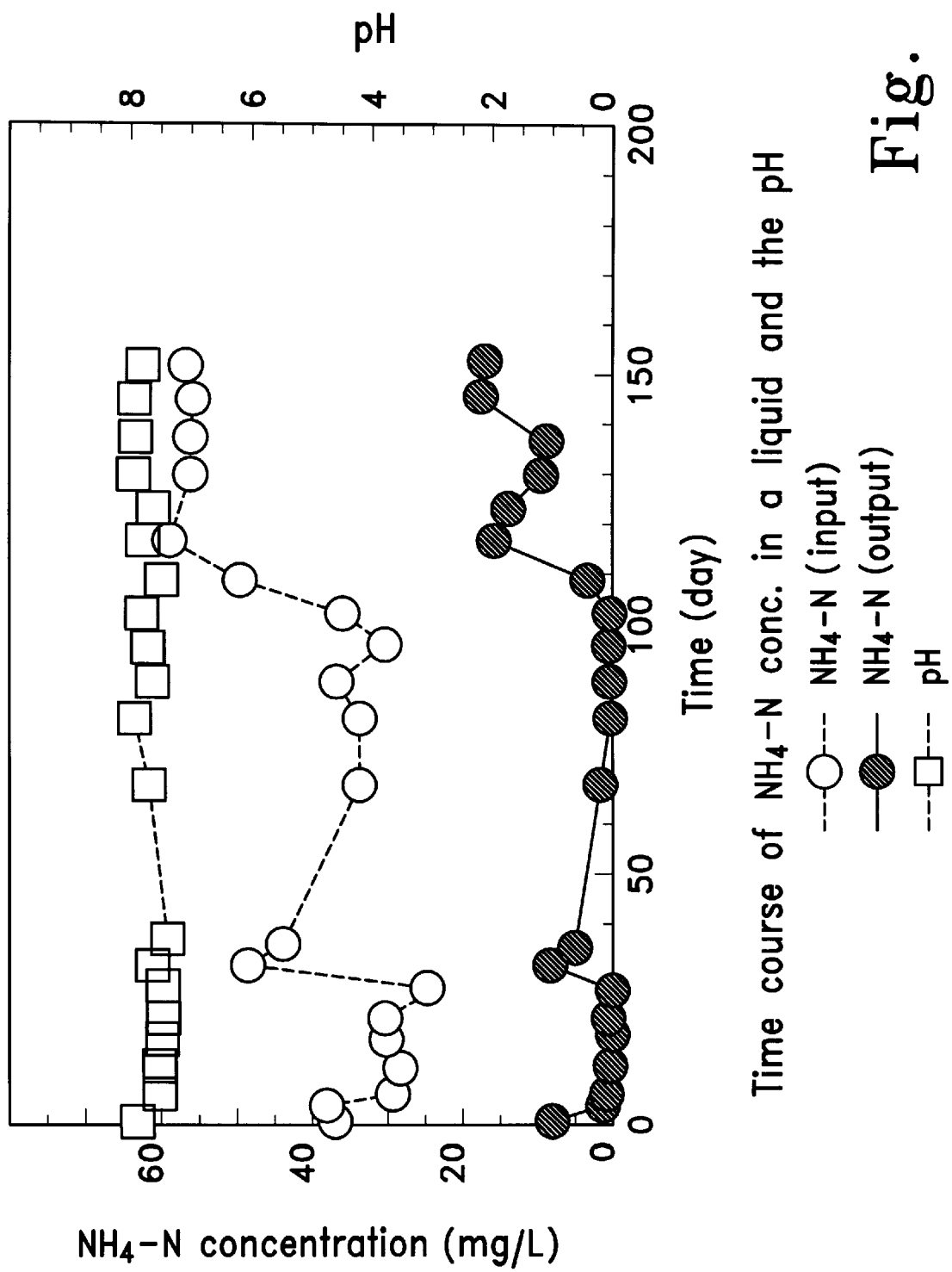
FIG. 13 is a graph showing the measurement of residual ammonia nitrogen ($NH_4$-N) in a nitrification tank in which nitrification treatment was conducted using a carrier having a pore diameter of 500 μm.

A nitrification test was conducted for 150 days in the same manner as in Example 15, except that the carrier obtained in Example 6 was used. The results obtained are shown in FIG. 13.

EXAMPLE 19

Figure 14:
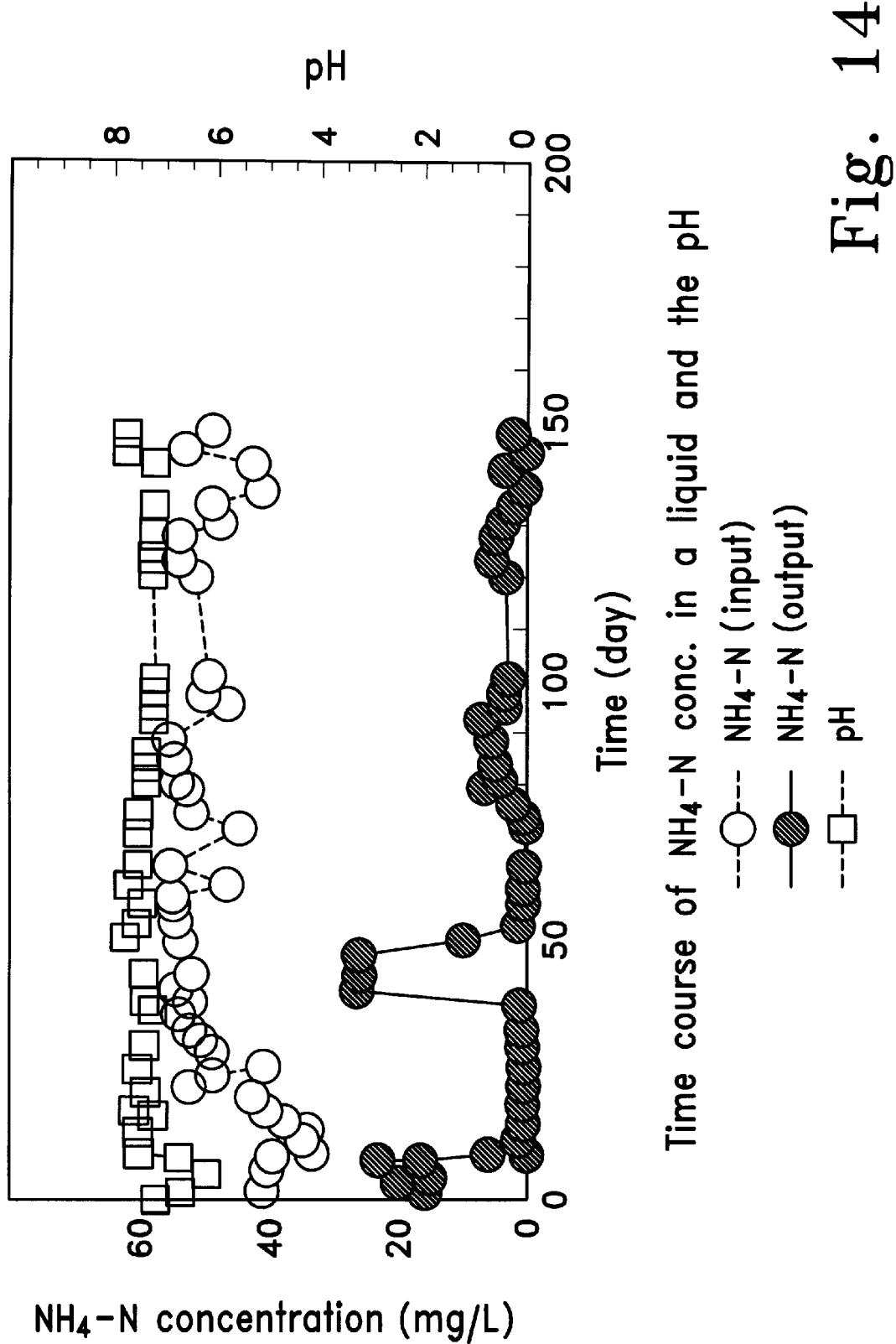
FIG. 14 is a graph showing the measurement of residual ammonia nitrogen ($NH_4$-N) in a liquid which was subjected to nitrification treatment using a carrier having a pore diameter of 1,260 μm.

A nitrification test was conducted for 150 days in the same manner as in Example 15, except the carrier obtained in Example 7 was used. The results obtained are shown in FIG. 14.

It is apparent from FIG. 11 that the ammonia nitrogen ($NH_4$-N) that was introduced could be converted with high efficiency. It is also apparent from FIGS. 12, 13 and 14 that the ammonia nitrogen ($NH_4$-N) in the liquid can be converted with high efficiency even using carriers having different pore sizes.

Denitrification Test: Conversion of Nitrogen Compounds Contained in a Liquid in a Denitrification Tank Under Anaerobic Conditions Using Carrier Comprising the Porous Cellulose Derivative A nitrogen compound, nitrate nitrogen ($NO_3$-N), in a liquid was converted using the liquid treatment tanks as shown in FIGS. 1, 3 and 5 as the denitrification tank, and the residual amount of nitrate nitrogen was measured. The details thereof are described by referring to Examples 20 to 23 described below.

EXAMPLE 20

The tower-like gas lift-type liquid treatment tank (volume of 1.3 liters) as shown in FIG. 1 was used as the denitrification tank. Conversion of microorganisms in the liquid was conducted in the tank while adjusting the maximum treatment amount in one day to 2.8 liters. The amount of acetic acid was 20 mM per mole of the carbon source in the liquid to be treated.

Figure 15:
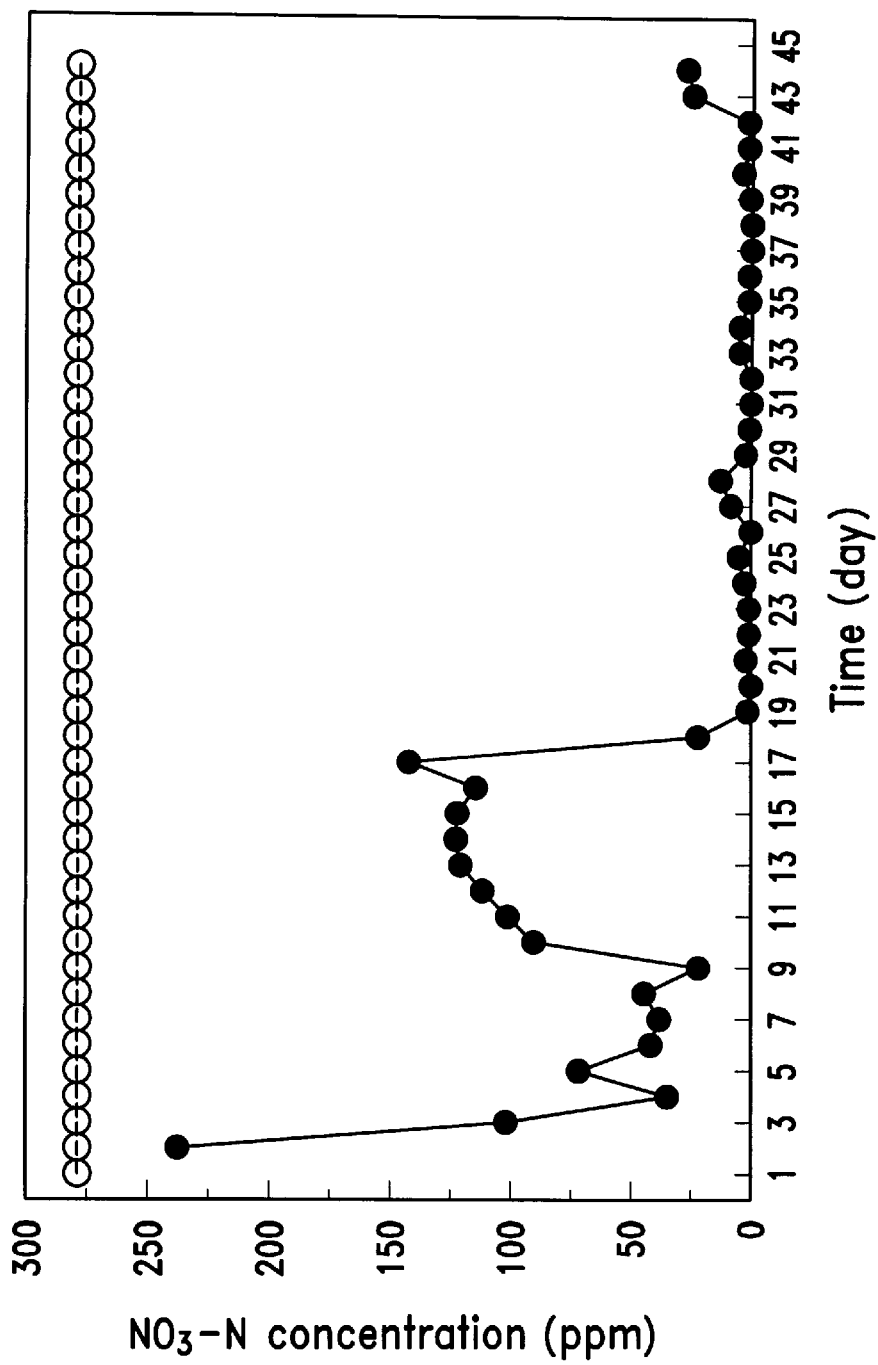
FIG. 15 is a graph showing the measurement of residual nitrate ammonia ($NO_3$-N) in a liquid which was subjected to denitrification treatment using the tower-like gas lift-type liquid treatment tank.

An artificially synthesized inorganic wastewater having compositions shown in Table 3 below was prepared as the liquid to be treated; acetic acid was supplied such that the concentration of nitrate nitrogen ($NO_3$-N) was 280 ppm. Activated sludge was adsorbed and immobilized onto the porous cellulose derivative obtained in Example 12 to prepare the carrier. The artificially synthesized wastewater prepared above was treated with the carrier in the denitrification tank for 45 days. The residual amount of nitrate nitrogen ($NO_3$-N) in the liquid was measured. The carrier comprising the porous cellulose derivative was introduced into the tank in the amount of 10 vol % based on the volume of the tank. The results obtained are shown in FIG. 15. The treatment capacity of the carrier was 56 mg-N/l-carrier/hr.

EXAMPLE 21

The downward-flowing expanding-type liquid treatment tank (volume 0.6 liter) was used as the denitrification tank. Conversion of microorganisms in the liquid was conducted while adjusting the maximum treatment amount in one day to 1.3 liters. The concentration of methanol was 40 mM per mole of the carbon source in the liquid to be treated.

Figure 16:
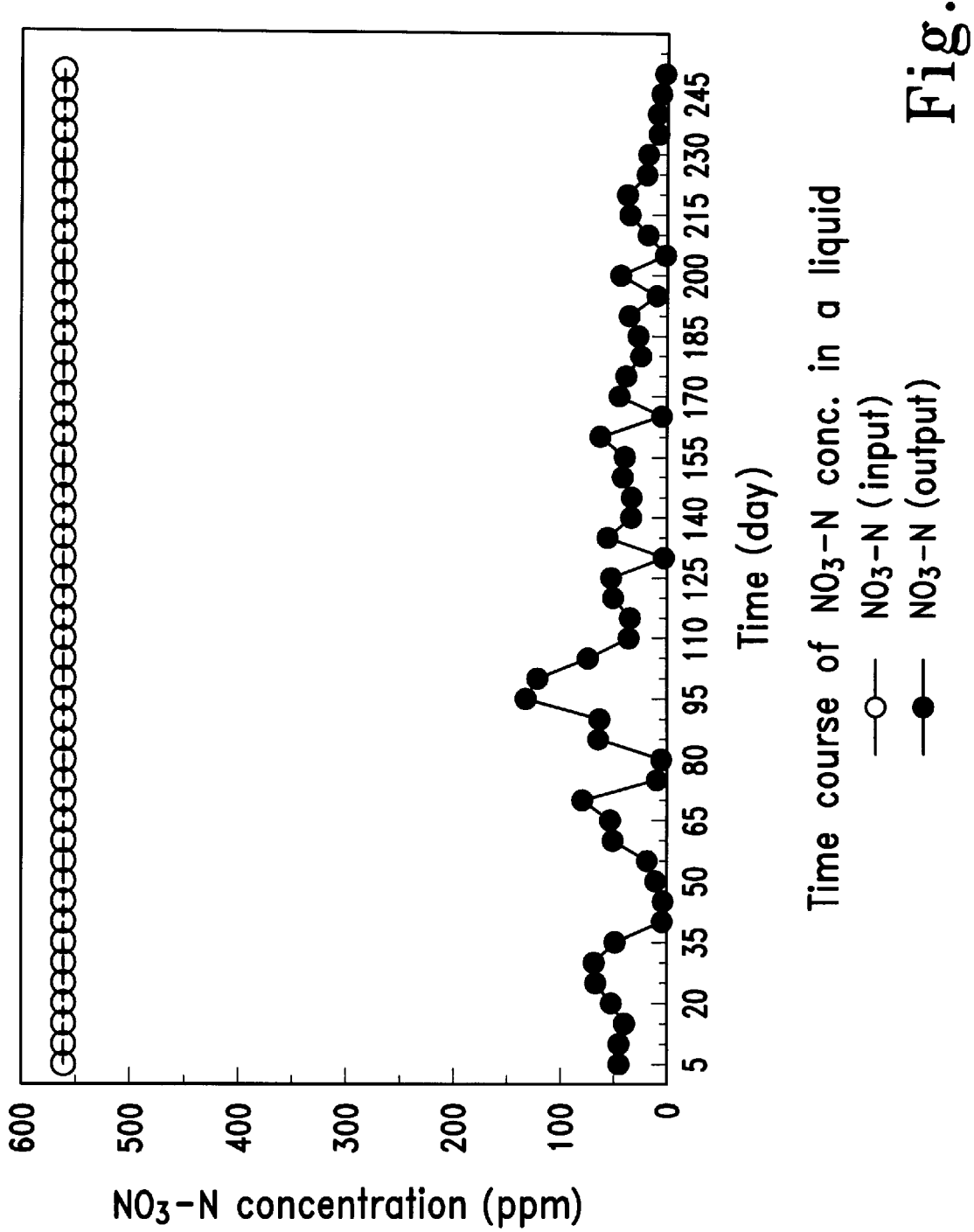
FIG. 16 is a graph showing the measurement of residual nitrate ammonia ($NO_3$-N) in a liquid which was subjected to denitrification treatment using a downward-flowing expanding-type liquid treatment tank.

An artificially synthesized inorganic wastewater having compositions shown in Table 3 below was prepared as the liquid to be treated; nitric acid was supplied such that the concentration of nitrate nitrogen ($NO_3$-N) was 560 ppm. Activated sludge was adsorbed and immobilized onto the porous cellulose obtained in Example 12 to prepare the carrier. The artificially synthesized wastewater prepared above was treated with the carrier in the tank for 245 days. The residual amount of nitrate nitrogen ($NO_3$-N) in the liquid was measured. The carrier comprising the porous cellulose derivative was introduced into the tank in the amount of 10 vol% based on the volume of the tank. The results obtained are shown in FIG. 16. The treatment capacity of the carrier was 508 mg-N/l-carrier/hr.

TABLE 3

| Compositions | Amount (in 1,000 ml) |
|---|---|
| $Na_2HPO_4$ | 7.9 g |
| $K_2HPO_4$ | 1.5 g |
| $MgSO_4 \cdot 7H_2O$ | 0.1 g |
| Trace element [1] | 2.0 ml |

[1] Trace elements (in 1,000 ,ml)
| | |
|---|---|
| EDTA | 5.00 g |
| $ZnSO_4 \cdot 7H_2O$ | 2.20 g |
| $CaCl_2$ | 5.54 g |
| $MnCl_2 \cdot 4H_2O$ | 5.06 g |
| $FeSO_4 \cdot 7H_2O$ | 4.99 g |
| $(NH_4)_6MO_7O_{24} \cdot 4H_2O$ | 1.10 g |
| $CuSO_4 \cdot 5H_2O$ | 1.57 g |
| $CoCl_2$ | 1.61 g |

EXAMPLE 22

Figure 17:
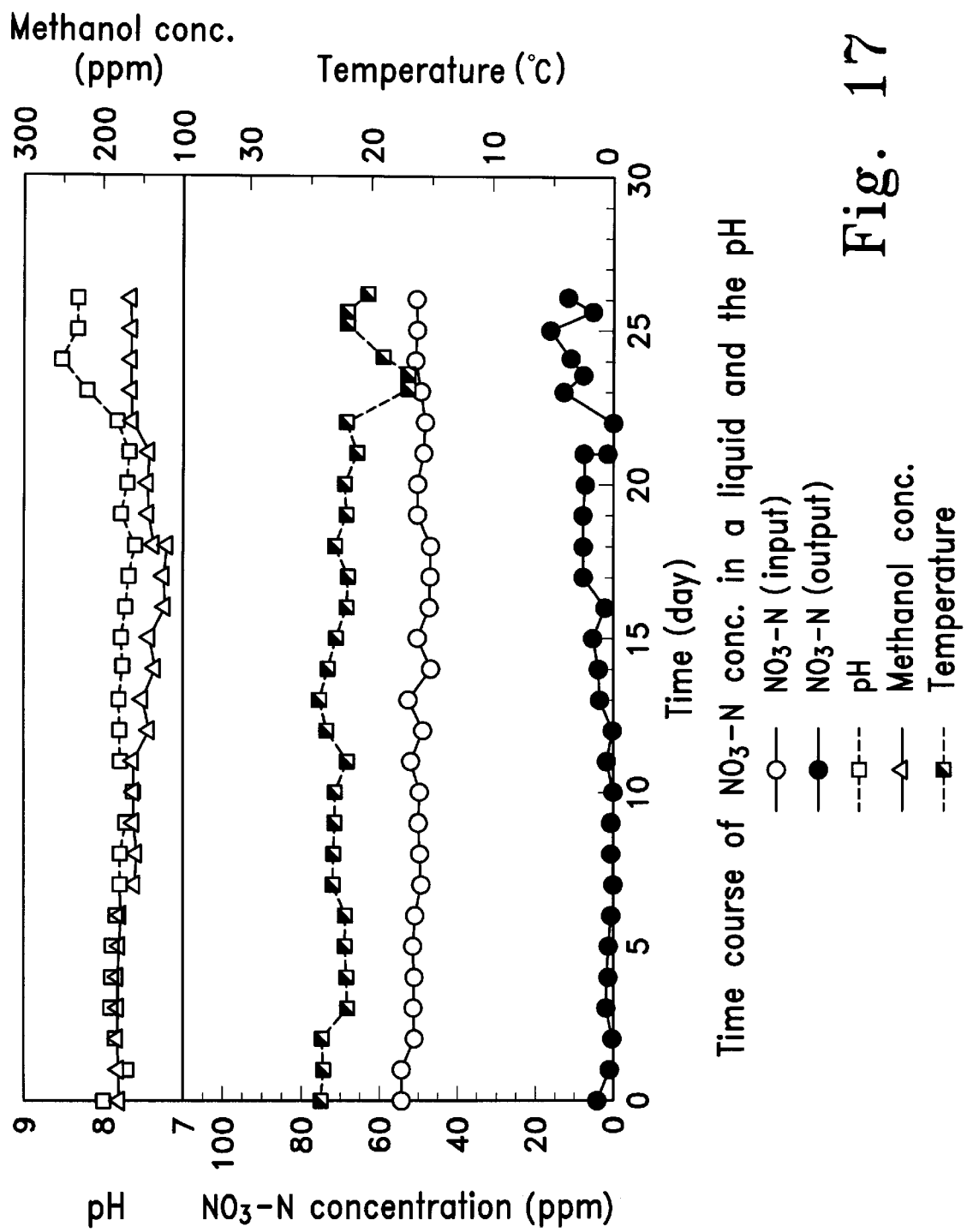
FIG. 17 is a graph showing the measurement of residual nitrate ammonia ($NO_3$-N) in a liquid which was subjected to denitrification treatment using the ejector-type liquid treatment tank.

An ejector-type liquid treatment tank (volume 15 liters) as shown in FIG. 5 was used as the denitrification tank. The maximum treatment amount was adjusted to 360 liters per day. Activated sludge was adsorbed and immobilized onto the porous cellulose obtained in Example 12 to prepare the carrier. Groundwater was used as the liquid to be treated. Denitrification treatment of groundwater was conducted with the carrier in the tank; nitric acid was supplied such that the concentration of nitrate nitrogen ($NO_3$-N) in the groundwater was 50 ppm. Further, methanol was introduced into the tank through an inlet for carbon source; according to need, hydrochloric acid was introduced into the tank through an inlet for inorganic compound in order to maintain the pH in the tank at 8.0. The treatment was conducted while circulating the liquid to be treated and the carrier with a flow current jet device. The carrier was introduced into the tank in the amount of 16 vol % based on the volume of the tank. The results obtained are shown in FIG. 17. The treatment capacity of the carrier was 312 mg-N/l-carrier/hr.

It is apparent from FIGS. 15, 16 and 17 that nitrate nitrogen ($NO_3$-N) in the liquid was converted with high efficiency.

The present invention relates to a carrier for immobilizing microorganisms, comprising a porous cellulose derivative or a porous cellulose, and a method of converting nitrogen compounds contained in a liquid using the carrier, where at least one member selected from an epoxy compound having an epoxy group, an N-methylol compound, a carbonyl compound, an acetal compound, an active vinyl compound, an aziridinyl compound, an aldehyde compound having an aldehyde group, a compound having an acyl group, a quaternary ammonium compound, an amidophosphazene compound, and a compound having an isocyanate group crosslinks glucose constituents of cellulose. Because the the disintegration of the cellulose by enzymes in microorganisms that degrade cellulose is thereby reduced, the carrier can be used over a long period of time.

Further, the carrier for immobilizing microorganisms, comprising a porous cellulose having coated thereon a compound obtained by reacting an epoxy compound with a polyamine compound, protects the cellulose with a coating of the compound; this coating makes it difficult for microorganisms to contact the carrier and thus prevents degradation of the cellulose. Because the degradation of the cellulose can be controlled, the carrier can be used over a long period of time. When the carrier for immobilizing microorganisms, comprising the porous cellulose derivative, is introduced into a liquid treatment tank such as a nitrification treatment tank or a denitrification treatment tank together with a liquid to be treated, and the resulting mixture is stirred, large quantities of microorganisms are immobilized onto the porous cellulose derivative due to the inherent characteristics of the cellulose. Because the activity of the microorganisms can be maintained, the treatment capacity of the carrier can be increased.

Further, when the carrier for immobilizing microorganisms comprising a porous cellulose, is introduced into a liquid treatment tank such as a nitrification treatment tank or a denitrification treatment tank together with the liquid to be treated, and the resulting mixture is stirred, cationic charges possessed by the compound obtained by reacting an epoxy compound with a polyamine compound enables the immobilization of a large amount of microorganisms onto the carrier. Because the density of the immobilized microorganisms is increased, the treatment capacity of the carrier can be increased.

In addition, since the cellulose used is a natural material, the carrier can be incinerated similar to paper; even if the carrier is embedded in the earth, the cellulose disintegrates with the passage of time. Thus, the carrier can easily be disposed after its use. While the invention has been described in detail and with reference to specific examples thereof, it will be apparent to one skilled in the art that various changes and modifications can be made therein without departing from the spirit and scope thereof.

We claim:

1. A carrier for immobilizing microorganisms, comprising a coated porous cellulose derivative obtained by reacting a porous cellulose with at least one member selected from the group consisting of an N-methylol compound, an imidazolidinone compound, an aldehyde compound having an aldehyde group, an acetal compound, an active vinyl compound, an aziridinyl compound, a compound having a carboxyl group, a compound having an acyl group, a compound having an isocyanate group and an amidophosphazene compound, and coating the resultant porous cellulose derivative with a compound obtained by reacting an epoxy compound having an epoxy group with a polyamine compound, wherein the epoxy compound is selected from the group consisting of glycidol, glycerol diglycidyl ether, glycerol triglycidyl ether, polyglycerol polyglycidyl ether, polyethylene glycol diglycidyl ether, ethylene glycol diglycidyl ether, polypropylene glycol diglycidyl ether, sorbitol polyglycidyl ether, sorbitan diglycidyl ether, bis-(2,3-epoxycyclopentyl)-ether, vinylcyclohexanedioxide, butadienediepoxide, 1,2-bis-(2,3-epoxy-2-methylpropoxy)-ethane, and 1,1,3-tris-(2,3-epoxy-propoxy)-butane.

2. A carrier for immobilizing microorganisms as claimed in claim 1, wherein the polyamine compound is selected from the group consisting of polyethyleneimine, polyallylamine, and polyvinylamine.

3. A carrier for immobilizing microorganisms as claimed in claim 1, wherein the polyamine compound is reacted with the epoxy compound in an amount ranging from 20 to 150% by weight based on the weight of the epoxy compound.

4. A carrier for immobilizing microorganisms as claimed in claim 1, wherein the polyamine compound is reacted with the epoxy compound in an amount ranging from 20 to 150% by weight based on the weight of the epoxy compound.

5. A carrier for immobilizing microorganisms as claimed in claim 2, wherein the polyamine compound is reacted with the epoxy compound in an amount ranging from 20 to 150% by weight based on the weight of the epoxy compound.

6. A carrier for immobilizing microorganisms as claimed in claim 1, wherein the compound obtained by reacting the epoxy compound with the polyamine compound is coated on the porous cellulose derivative in an amount ranging from 10 to 60% by weight based on the weight of the porous cellulose derivative.

7. A carrier for immobilizing microorganisms as claimed in claim 3, wherein the compound obtained by reacting the epoxy compound with the polyamine compound is coated on the cellulose in an amount ranging from 10 to 60% by weight based on the weight of the cellulose.

8. A carrier for immobilizing microorganisms as claimed in claim 1, wherein the N-methylol compound is at least one member selected from the group consisting of dimethylolurea (DMU), methylated trimethylolmelamine (MTMM), dimethylolethylene urea (DMEU), dimethylolmethyl triazone (DMTr), dimethylolethyl triazone, dimethylolhydroxyethyl triazone, methylated dimethylol urone (DMUr), hexamethylol melamine (HMM), dimethylolpropylene urea (DMPU), dimethyloldihydroxyethylene urea (DMDHEU), tetramethylolacetylene diurea (TMADU), 4-methoxy-5-dimethylpropylene urea dimethylol compound (4MO, 5DM, PU), dimethylolmethyl carbamate (DMAC), dimethylolethyl carbamate dimethylolhydroxyethyl carbamate, dimethylolhydroxyisopropyl carbamate, dimethyloldimethoxyethylene urea, dimethylolbutylene urea, dimethylol-5-hydroxypropylene urea, dimethylol urone, and tetramethylolethylene bistriazone.

9. A carrier for immobilizing microorganisms as claimed in claim 1, wherein the imidazolidinone compound is at least one member selected from the group consisting of 4,5-dihydroxy-imidazolidinone, 1,3-dimethyl-4,5-dihydroxy-2-imidazolidinone, 1,3-diethyl-4,5-dihydroxy-2-imidazolidinone, 1,3-dipropyl-4,5-dihydroxy-2-imidazolidinone, 1,3-di(α-dihydroxyethyl)-4,5-dihydroxy-2-imidazolidinone, 1,3-di(β-dihydroxyethyl)-4,5-dihydroxy-2-imidazolidinone, 1,3-dimethyl-4,5-dimethoxy-2-imidazolidinone, 1,3-dimethyl-4,5-diethoxy-2-imidazolidinone, 1,3-dimethyl-4,5-diisopropoxy-2-imidazolidinone, 1,3-dimethyl-4,5-diacetoxy-2-imidazolidinone, 1,3-di-(β-cyanoethyl)-4,5-dihydroxy-2-imidazolidinone, 1,3-di-(β-cyanoethyl)-4,5-dimethoxy-2-imidazolidinone, 1,3-di-(β-carbamoylethyl)-4,5-dihydroxy-2-imidazolidinone, 1,3-di-(β-carbamoylethyl)-4,5-dimethoxy-2-imidazolidinone, 1,3-di-(β-carboxyethyl)-4,5-dihydroxy-2-imidazolidinone, 1,3-di-(P-carboxyethyl)-4,5-dimethoxy-2-imidazolidinone, 1,3-di-(β-ethoxycarbonylethyl)-4,5-dihydroxy-2-imidazolidinone, and 1,3-di-(β-ethoxycarbonylethyl)-4,5 -dimethoxy-2-imidazolidinone.

10. A carrier for immobilizing microorganisms as claimed in claim 1, wherein the aldehyde compound is at least one member selected from the group consisting of a compound formaldehyde, glyoxal, acetaldehyde, a compound obtained by reacting cyclic urea with glyoxal, acrylic aldehyde, and a compound obtained by reacting acrylic amide with glyoxal.

11. A carrier for immobilizing microorganisms as claimed in claim 1, wherein the acetal compound is at least one member selected from the group consisting of glycol acetal and pentaerythritol bisacetal.

12. A carrier for immobilizing microorganisms as claimed in claim 1, wherein the active vinyl compound is at least one member selected from the group consisting of methacrylic acid hydroxy-propyltrimethyl-ammonium chloride, glycerol dimethacrylate, glycerol methacrylate acrylate, glycerol methacrylate alkenylate, diethylene glycol dimethacrylate, trimethylolpropane trimethacrylate, and zinc diacrylate.

13. A carrier for immobilizing microorganisms as claimed in claim 1, wherein the amidophosphazene is at least one member selected from the group consisting of an aminodiethylamidophosphazene oligomer, a tetraamino-di-n-propoxycyclotriphosphazene, and penta-amino-monophenoxycyclotriphosphazene.

14. A carrier for immobilizing microorganisms according to claim 1, wherein the porous cellulose is foamed cellulose.

15. A carrier for immobilizing microorganisms as claimed in claim 14, wherein the compound reacted with the foamed cellulose is in an amount ranging from 3 to 60% by weight based on the weight of the foamed cellulose.

16. A carrier for immobilizing microorganisms as claimed in claim 8, wherein the compound reacted with cellulose is in an amount ranging from 3 to 60% by weight based on the weight of the cellulose.

17. A carrier for immobilizing microorganisms as claimed in claim 9, wherein the compound reacted with cellulose is in an amount ranging from 3 to 60% by weight based on the weight of the cellulose.

18. A carrier for immobilizing microorganisms as claimed in claim 10, wherein the compound reacted with cellulose is in an amount ranging from 3 to 60% by weight based on the weight of the cellulose.

19. A carrier for immobilizing microorganisms as claimed in claim 11, wherein the compound reacted with cellulose is in an amount ranging from 3 to 60% by weight based on the weight of the cellulose.

20. A carrier for immobilizing microorganisms as claimed in claim 12, wherein the compound reacted with cellulose is in an amount ranging from 3 to 60% by weight based on the weight of the cellulose.

21. A carrier for immobilizing microorganisms as claimed in claim 13, wherein the compound reacted with cellulose is in an amount ranging from 3 to 60% by weight based on the weight of the cellulose.

22. A carrier for immobilizing microorganisms as in claim 14, wherein the foamed cellulose has a pore diameter ranging from 30 to 2000 μm.

23. A carrier for immobilizing microorganisms as claimed in claim 1, wherein the porous cellulose has a pore diameter ranging from 30 to 2000 μm.

24. A method of converting nitrogen compounds in a liquid, which comprises introducing the carrier for immobilizing microorganisms as claimed in claim 1 into a liquid treatment tank together with a liquid to be treated, immobilizing microorganisms on the carrier, and stirring the resulting mixture in the tank, thereby converting the nitrogen compounds contained in the liquid to be treated.

25. A method according to any on of claims 24, wherein the liquid in the liquid treatment tank is under anaerobic conditions.

26. A method of converting nitrogen compounds in a liquid, which comprises introducing the carrier for immobilizing microorganisms as claimed in claim 1 into a first treatment tank under aerobic conditions and a denitrification treatment tank under anaerobic conditions together with a liquid to be treated, immobilizing microorganisms on the carrier, stirring the resulting mixtures in the tanks, flowing the entire liquid to be treated from the first treatment tank under aerobic conditions to the denitrification treatment tank under anaerobic conditions, thereby converting the nitrogen compounds contained in the liquid to be treated.

27. A method of converting nitrogen compounds in a liquid, which comprises introducing the carrier for immobilizing microorganisms as claimed in claim 1 into a first treatment tank under aerobic conditions and a denitrification treatment tank under anaerobic conditions together with a liquid to be treated, immobilizing microorganisms on the carrier, stirring the resulting mixtures, flowing the entire amount of the liquid to be treated from the denitrification tank under anaerobic conditions to the first treatment tank under aerobic conditions, and circulating part of the liquid to be treated between the denitrification treatment tank under anaerobic conditions and the first treatment tank under aerobic conditions, thereby converting the nitrogen compounds contained in the liquid to be treated.

28. A method of converting nitrogen compounds in a liquid as claimed in any one of claims 24, 25, 26 and 27, wherein the cellulose derivative is introduced into the treatment tank in an amount ranging from 3 to 100% by volume based on the volume of the treatment tank.

29. A method of converting nitrogen compounds in a liquid as claimed in any one of claims 24, 25, 26 and 27, wherein the liquid is potable water or wastewater.

30. A method of converting nitrogen compounds in a liquid as in claim 28, wherein the liquid is wastewater.

31. A method of converting nitrogen compounds in a liquid as in claim 28, wherein the liquid is potable water.

* * * * *